(12) United States Patent
Katabuchi et al.

(10) Patent No.: US 9,592,213 B2
(45) Date of Patent: Mar. 14, 2017

(54) PROPHYLACTIC AND/OR THERAPEUTIC AGENT FOR DYSMENORRHEA

(75) Inventors: Hidetaka Katabuchi, Kumamoto (JP); Ritsuo Honda, Kumamoto (JP); Hideyuki Saya, Tokyo (JP); Yoshimi Arima, Tokyo (JP); Shinichiro Niwa, Tokyo (JP); Yasutaka Makino, Tokyo (JP)

(73) Assignees: National University Corporation Kumamoto University, Kumamoto (JP); Keio University, Tokyo (JP); Link Genomis, Inc., Tokyo (JP)

( * ) Notice: Subject to any disclaimer, the term of this patent is extended or adjusted under 35 U.S.C. 154(b) by 0 days.

(21) Appl. No.: 13/378,481

(22) PCT Filed: Jun. 17, 2010

(86) PCT No.: PCT/JP2010/060301
§ 371 (c)(1),
(2), (4) Date: Mar. 2, 2012

(87) PCT Pub. No.: WO2010/147184
PCT Pub. Date: Dec. 23, 2010

(65) Prior Publication Data
US 2012/0157535 A1 Jun. 21, 2012

(30) Foreign Application Priority Data
Jun. 17, 2009 (JP) ................. 2009-144145

(51) Int. Cl.
*A61K 31/196* (2006.01)
(52) U.S. Cl.
CPC ................. *A61K 31/196* (2013.01)
(58) Field of Classification Search
CPC .............. A61K 31/195; A61K 31/196
See application file for complete search history.

(56) References Cited

U.S. PATENT DOCUMENTS

| 5,385,935 | A * | 1/1995 | Tamai | A61K 31/19 514/535 |
| 6,407,139 | B1 | 6/2002 | Isaji et al. | |
| 6,552,083 | B1 | 4/2003 | Isobe et al. | |
| 2004/0024016 | A1 | 2/2004 | Sugamata | |
| 2007/0262022 | A1 | 11/2007 | Mosler et al. | |
| 2009/0197957 | A1 | 8/2009 | Selley et al. | |
| 2010/0158905 | A1* | 6/2010 | Pearlman | A61K 31/192 424/133.1 |

FOREIGN PATENT DOCUMENTS

| CN | 101222918 A | 7/2008 | | |
| DE | WO 0115679 A2 * | 3/2001 | ......... | A61K 31/57 |
| EP | 0 894 496 A1 | 2/1999 | | |
| EP | 1 197 210 B1 | 4/2002 | | |
| JP | 05-163222 A | 6/1993 | | |
| JP | 06-135829 A | 5/1994 | | |
| JP | 07-277966 A | 10/1995 | | |
| JP | 09-227371 A | 9/1997 | | |
| JP | 2002-187855 A | 7/2002 | | |
| JP | 2003-508544 A | 3/2003 | | |
| WO | WO 97/29744 A1 | 8/1997 | | |
| WO | WO 01/05934 A2 | 1/2001 | | |
| WO | WO 01/13911 A1 | 3/2001 | | |
| WO | WO 01/13952 A1 | 3/2001 | | |
| WO | WO 01/18040 A2 | 3/2001 | | |
| WO | WO 2005/092464 A1 | 10/2005 | | |
| WO | WO 2006/122353 A1 | 11/2006 | | |

OTHER PUBLICATIONS

Suzawa, H. "Inhibitory action of tranilast, an anti-allergic drug, on the release of cytokines and PGE2 from human monocytes-macrophages" 1992, 60, 85-90.*
Analgesic definition (http://dictionary.reference.com/browse/analgesic) accessed Jan. 27, 2015.*
Inglis, J.J.; Criado, G.; Andrews, M.; Feldmann, M.; Williams, R.O.; Selley, M.L. "The anti-allergic drug, N-(30,40-dimethoxycinnamonyl) anthranilic acid, exhibits potent anti-inflammatory and analgesic properties in arthritis" Rheumatology 2007, 46, 1428-1432.*
Jordana, M.; Sarnstrand, B.; Sime, P.J.; Ramis, I. "Immune-inflammatory functions of fibroblasts" Eur. Respir. J. 1994, 7, 2212-2222.*
Costa, M.A.; Simon, D.I. "Molecular Basis of Restenosis and Drug-Eluting Stents" Circulation 2005, 111, 2257-2273.*
"Prevent" definition (http://www.merriam-webster.com/dictionary/prevent) accessed Jul. 8, 2015.*
Secondary Dysmenorrhea (http://www.menstruation-info-with-doc.com/secondary-dysmenorrhea.html) accessed Feb. 19, 2016.*
Jabbour, H.N. et al. "Prostaglandin receptors are mediators of vascular function in endometrial pathologies" 2006, 252, 191-200.*
Pae, H-O.; Jeong, S-O., Koo, B.S.; Ha, H-Y.; Lee, K-M.; Chung, H-T. Biochemical and Biophysical Research Communications 2008, 371, 361-365.*
Spiecker, M.; Lorenz, I.; Marx, N.; Darius, H. "Tranilast Inhibits Cytokine-Induced Nuclear Factor kB Activation in Vascular Endothelial Cells" Mol Pharm 2002, 62, 4, 856-863.*
French, L. "Dysmenorrhea in Adolescents" Pediatr Drugs 2008, 10 (1), 1-7.*
Inoue, H. at al. "Suppressive Effects of Tranilast on the Expression of Inducible Cyclooxygenase (COX2) in Interleukin-1 B-Stimulated Fibroblasts" Biochemical Pharmacology, vol. 53, pp. 1941-1944, 1997.*

(Continued)

*Primary Examiner* — Timothy Thomas
*Assistant Examiner* — Andrew S Rosenthal
(74) *Attorney, Agent, or Firm* — Foley & Lardner LLP

(57) ABSTRACT

Disclosed is a prophylactic and/or therapeutic agent for dysmenorrhea and/or associated symptoms thereof. Specifically disclosed is a prophylactic and/or therapeutic agent for dysmenorrhea and/or associated symptoms thereof, which comprises tranilast as an active ingredient thereof.

5 Claims, 14 Drawing Sheets
(3 of 14 Drawing Sheet(s) Filed in Color)

(56) References Cited

OTHER PUBLICATIONS

Capper, E.A. et al. "Modulation of Human Monocyte Activities by Tranilast, SB 252218, a Compound Demonstrating Efficacy in Restenosis" J. Pharmacol. Exp. Ther. 2000, 295, 1061-1069.*

Shime, H. et al. "Tranilast Inhibits the Proliferation of Uterine Leiomyoma Cells in Vitro through G1 Arrest Associated with the Induction of p21waf1 and p53" The Journal of Clinical Endocrinology & Metabolism 2002, 87(12):5610-5617.*

Chakrabarti, R. et al. "Tranilast inhibits the growth and metastasis of mammary carcinoma" Anti-Cancer Drugs 2009, 20:334-345.*

Grund et al., "Tumor Necrosis Factor-α Regulates Inflammatory and Mesenchymal Responses via Mitogen-Activated Protein Kinase Kinase, p. 38, and Nuclear Factor κb in Human Endometriotic Epithelial Cells," Molecular Pharmacology, 2008, 73(5)1 394-1404.

Harel et al., "Original Studies: The Use of the Leukotriene Receptor Antagonist Montelukast (Singulair®) in the Management of Dysmenorrhea in Adolescents," J. Pediatr. Adolesc. Gynecol., 2004, 17:183-186.

Honda et al., "Special Feature/Lower back pain—All about Ambulatory Practice," Japanese Journal of Clinical and Experimental Medicine, Mar. 2003, 80(3):35(417)-38(420), with English translation, 8 pages.

International Statistical Classification of Diseases and Related Health Problems 10th Revision Version for 2007, Chapter XIV: Diseases of the genitourinary system (N00-N99), 7 pages.

Jones et al., "Long-Term Follow-Up of a Controlled Trial of Laser Laparoscopy for Pelvic Pain," JSLS, 2001, 5:111-115.

Kaneyama et al., "Analysis of Suppressive Effect of Tranilast on Tubular Epithelial EMT in UUO Rats," The Japanese Journal of Nephrology, Apr. 25, 2009, 51(3):267, Feb. 9, 2012, with English translation.

Kashimura, Masamichi, "Special Feature/Smart Pain Control: Menorrhalgia," Japanese Journal of Clinical and Experimental Medicine, Mar. 2001, 78(3):47-50, with English translation, 10 pages.

Kawamura et al., "Recent Concepts of Uterine Leiomyoma, 1. Introduction: Characteristics, Natural History and Operation-Indication of Uterine Leiomyoma," Obstetrical and Gynecological Therapy, Aug. 2000, 81(2):210-214, with English translation, 9 pages.

Lippman et al., "Uterine fibroids and gynecologic pain symptoms in a population-based study," Fertility and Sterility, Dec. 2003, 80(6):1488-1494.

Miyatake et al., "Diagnosis and Treatment of Dysmenorrhea," Modem Physician, 2009, 29(3):398-399, with English translation, 4 pages.

Nuttall et al., "The Effect of Norethisterone (500 mcg) and ethinyl estradiol (35 mcg) capsules on the pituitary-ovarian axis," Contraception, May 1982, 25(5):463-469.

Neilson, Eric G., "Setting a trap for tissue fibrosis," Nature Medicine, Apr. 2005, 11(4):373-374.

Saegusa et al., "Requirement of the Akt/β-Catenin Pathway for Uterine Carcinosarcoma Genesis, Modulating E-Cadherin Expression Through the Transactivation of Slug," The American Journal of Pathology, Jun. 2009, 174(6):2107-2115.

Shime et al., "Tranilast Inhibits the Proliferation of Uterine Leiomyoma Cells in Vitro through G1 Arrest Associated with the Induction of p21$^{waf1}$ and p53," The Journal of Clinical Endocrinology & Metabolism, 2002, 87(12):5610-5617.

Takahashi et al., "Feature: Early Cancer Detection, Complaint and Symptoms that Should not be Overlooked," Journal of Therapy, Jan. 2008, 90(1):40-44, with English translation, 9 pages.

Tamaya, Teruhiko, "Studies on Endometriosis—update," EBM and TBM in Endometriosis, 2003, 86(6):1105-1111, with English translation, 13 pages.

\* cited by examiner

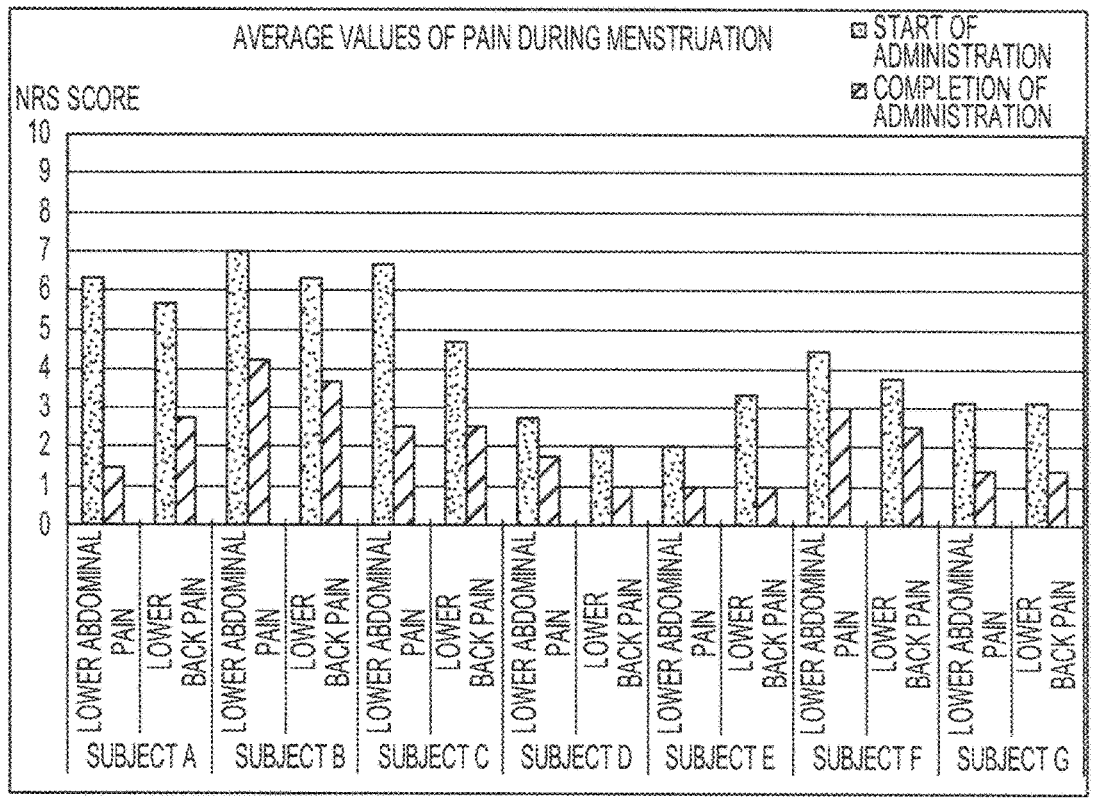

FIG. 8A

| | EVALUATED PARAMETER | PAIN SCORE IMPROVEMENT RATE |
|---|---|---|
| SUBJECT A | LOWER ABDOMINAL PAIN | 76% |
| | LOWER BACK PAIN | 51% |
| SUBJECT B | LOWER ABDOMINAL PAIN | 40% |
| | LOWER BACK PAIN | 42% |
| SUBJECT C | LOWER ABDOMINAL PAIN | 63% |
| | LOWER BACK PAIN | 46% |
| SUBJECT D | LOWER ABDOMINAL PAIN | 36% |
| | LOWER BACK PAIN | 50% |
| SUBJECT E | LOWER ABDOMINAL PAIN | 50% |
| | LOWER BACK PAIN | 70% |
| SUBJECT F | LOWER ABDOMINAL PAIN | 32% |
| | LOWER BACK PAIN | 33% |
| SUBJECT G | LOWER ABDOMINAL PAIN | 55% |
| | LOWER BACK PAIN | 55% |

| | PARAMETER | BEFORE START OF ADMINISTRATION | DURING FINAL EXAMINATION | |
|---|---|---|---|---|
| SUBJECT A | LOWER ABDOMINAL PAIN DURING MENSTRUATION | ☐ ---<br>☐ BEARABLE<br>☐ ANALGESIC<br>■ BEDRIDDEN | ☐ ---<br>☐ BEARABLE<br>■ ANALGESIC<br>☐ BEDRIDDEN | (AT EXAMINATION 6 MONTHS LATER) |
| | LOWER BACK PAIN DURING MENSTRUATION | ☐ ---<br>☐ BEARABLE<br>■ ANALGESIC<br>☐ BEDRIDDEN | ☐ ---<br>■ BEARABLE<br>☐ ANALGESIC<br>☐ BEDRIDDEN | (AT EXAMINATION 6 MONTHS LATER) |
| SUBJECT C | LOWER ABDOMINAL PAIN DURING MENSTRUATION | ☐ ---<br>☐ BEARABLE<br>☐ ANALGESIC<br>■ BEDRIDDEN | ☐ ---<br>☐ BEARABLE<br>■ ANALGESIC<br>☐ BEDRIDDEN | (AT EXAMINATION 5 MONTHS LATER) |
| | LOWER BACK PAIN DURING MENSTRUATION | ☐ ---<br>☐ BEARABLE<br>☐ ANALGESIC<br>■ BEDRIDDEN | ☐ ---<br>☐ BEARABLE<br>■ ANALGESI<br>☐ BEDRIDDEN | (AT EXAMINATION 5 MONTHS LATER) |
| SUBJECT D | LOWER ABDOMINAL PAIN DURING MENSTRUATION | ☐ ---<br>☐ BEARABLE<br>■ ANALGESIC<br>☐ BEDRIDDEN | ■ ---<br>☐ BEARABLE<br>☐ ANALGESIC<br>☐ BEDRIDDEN | (AT EXAMINATION 6 MONTHS LATER) |
| | LOWER BACK PAIN DURING MENSTRUATION | ☐ ---<br>☐ BEARABLE<br>■ ANALGESIC<br>☐ BEDRIDDEN | ■ ---<br>☐ BEARABLE<br>☐ ANALGESIC<br>☐ BEDRIDDEN | (AT EXAMINATION 6 MONTHS LATER) |
| SUBJECT E | LOWER ABDOMINAL PAIN DURING MENSTRUATION | ☐ ---<br>☐ BEARABLE<br>☐ ANALGESIC<br>■ BEDRIDDEN | ☐ ---<br>■ BEARABLE<br>☐ ANALGESIC<br>☐ BEDRIDDEN | (AT EXAMINATION 6 MONTHS LATER) |
| | LOWER BACK PAIN DURING MENSTRUATION | ☐ ---<br>☐ BEARABLE<br>☐ ANALGESIC<br>■ BEDRIDDEN | ☐ ---<br>■ BEARABLE<br>☐ ANALGESIC<br>☐ BEDRIDDEN | (AT EXAMINATION 6 MONTHS LATER) |
| SUBJECT F | LOWER ABDOMINAL PAIN DURING MENSTRUATION | ☐ ---<br>☐ BEARABLE<br>■ ANALGESIC<br>☐ BEDRIDDEN | ☐ ---<br>■ BEARABLE<br>☐ ANALGESIC<br>☐ BEDRIDDEN | (AT EXAMINATION 6 MONTHS LATER) |
| | LOWER BACK PAIN DURING MENSTRUATION | ☐ ---<br>☐ BEARABLE<br>■ ANALGESIC<br>☐ BEDRIDDEN | ☐ ---<br>■ BEARABLE<br>☐ ANALGESIC<br>☐ BEDRIDDEN | (AT EXAMINATION 6 MONTHS LATER) |
| SUBJECT G | LOWER ABDOMINAL PAIN DURING MENSTRUATION | ■ ---<br>☐ BEARABLE<br>☐ ANALGESIC<br>☐ BEDRIDDEN | ■ ---<br>☐ BEARABLE<br>☐ ANALGESIC<br>☐ BEDRIDDEN | (AT EXAMINATION 5 MONTHS LATER) |
| | LOWER BACK PAIN DURING MENSTRUATION | ■ ---<br>☐ BEARABLE<br>☐ ANALGESIC<br>☐ BEDRIDDEN | ■ ---<br>☐ BEARABLE<br>☐ ANALGESIC<br>☐ BEDRIDDEN | (AT EXAMINATION 5 MONTHS LATER) |

Fig. 11

| | PARAMETER | BEFORE START OF ADMINISTRATION | AT EXAMINATION 1 MONTH LATER |
|---|---|---|---|
| SUBJECT H | LOWER ABDOMINAL PAIN DURING MENSTRUATION | ○ ···<br>☐ BEARABLE<br>■ ANALGESIC<br>☐ BEDRIDDEN | ○ ···<br>■ BEARABLE<br>☐ ANALGESIC<br>☐ BEDRIDDEN |
| | LOWER BACK PAIN DURING MENSTRUATION | ○ ···<br>☐ BEARABLE<br>■ ANALGESIC<br>☐ BEDRIDDEN | ○ ···<br>■ BEARABLE<br>☐ ANALGESIC<br>☐ BEDRIDDEN |

PROPHYLACTIC AND/OR THERAPEUTIC AGENT FOR DYSMENORRHEA

CROSS-REFERENCE TO RELATED APPLICATIONS

This application is a National Stage application of PCT/JP2010/060301, filed Jun. 17, 2010, which claims priority from Japanese application JP 1009-144145, filed Jun. 17, 2009.

TECHNICAL FIELD

The present invention relates to a prophylactic and/or therapeutic agent for dysmenorrhea. More particularly, the present invention relates to a prophylactic and/or therapeutic agent for dysmenorrhea and/or associated symptoms thereof having as an active ingredient thereof tranilast, a derivative thereof or a salt thereof

BACKGROUND ART

Although 50% to 60% of women are said to experience some degree of pain associated with menstruation, intense menstrual pain requiring remaining in bed or recuperation and some form of medical accommodations is referred to as dysmenorrhea (Non-Patent Document 1). Dysmenorrhea is a syndrome extending from just before the start of menstruation through menstruation that mainly manifests itself with the primary complaints of lower abdominal pain and lower back pain, and is a gynecological disease that may be associated with various associated symptoms (including headache, menorrhagia and malaise).

Dysmenorrhea is a disease that is classified as N94 in the International Classifications of Disease ICD10 issued by the World Health Organization (WHO), and can further be classified into two types. These two types consist of functional (primary) dysmenorrhea (N94.4 in ICD10) and organic (secondary) dysmenorrhea (N94.5 in ICD10) (Non-Patent Document 2).

Functional (primary) dysmenorrhea is not associated with an organic disease in the pelvis, and 90% or more of dysmenorrhea is functional (primary) dysmenorrhea. With respect to the mechanism of onset of functional (primary) dysmenorrhea, although various theories have been advocated regarding the cause thereof, such as hypercontraction of uterine muscle, uterine ischemia, overproduction of prostaglandin F2α, hormone imbalance, poor circulation or psychological factors, the cause has yet to be fully determined and has yet to be identified (Non-Patent Document 1). On the other hand, although organic (secondary) dysmenorrhea is a disease that occurs as one of associated symptoms in the case a well-defined disease is present in the pelvis, such as pelvic congestion syndrome, intrapelvic infection, intrapelvic inflammatory disease, cervical stenosis, uterine myoma, endometrioma, uterine adenomyosis or positional and morphological anomalies of the uterus, it does not necessary occur due to the presence of these organic diseases, and the cause as to why dysmenorrhea occurs in these cases is not fully understood.

Since the lower abdominal pain and lower back pain during the onset of dysmenorrhea is extremely intense, many patients make accommodations by taking an analgesic for the purpose of temporary relief of that pain. Although examples of analgesics primarily include non-steroid anti-inflammatory drugs (NSAID) such as voltaren, ibuprofen or naproxen having cyclooxygenase inhibitory action, none of these have an action that specifically cures dysmenorrhea, but rather merely demonstrate effects in the form of symptomatic therapy that serves to temporarily alleviate pain associated with the disease (Non-Patent Documents 3, 4 and 5). Consequently, there are many cases that do not experience improvement in the level of pain or exacerbation due to progression of the disease state despite having taken such medication for many years. Moreover, analgesics have also been reported to have problems with adverse side effects, such as the occurrence of gastrointestinal disorders or renal disorders, due to long-term use. In the case of voltaren tablets, for example, adverse side effects have been observed to occur at a frequency of 10.85% according to the findings of a pre-approval study, and although these adverse side effects consist mainly of gastrointestinal symptoms such as stomachache, gastric discomfort or abdominal pain (9.43%), other adverse side effects include generalized systemic symptoms such as edema (0.95%) and skin symptoms such as itching and rash (1.56%) (Non-Patent Document 3). In this manner, despite these analgesics that are only taken when needed and do not demonstrate any therapeutic effects, as a result of being associated with numerous adverse side effects, there is a strong desire among patients and clinicians for the development of a therapeutic agent having few adverse side effects.

With respect to the treatment of dysmenorrhea, since the mechanism of occurrence is not fully understood for both functional and organic dysmenorrhea, an effective therapeutic agent has yet to be found. Consequently, in the current clinical setting, treatment is provided by either interrupting or reducing menstruation in serious cases since symptoms of dysmenorrhea always occur in association with menstruation. More specifically, treatment consists of administration of gonadotropins that inhibit the menstrual cycle, hormone preparations that inhibit the production and secretion of sex hormones, decrease ovarian function and induce endometrial atrophy, or low-dose oral contraceptives (pill). Since menstruation is interrupted or menstrual bleeding is reduced as a result of taking these drugs, pain associated with menstruation is considerably improved.

However, since hormone preparations and low-dose oral contraceptives do not treat the focus of dysmenorrhea, intense pain during menstruation frequently recurs when they are no longer taken and anovular menstruation resumes. Moreover, the presence of numerous adverse side effects is also a problem with respect to hormone preparations and low-dose oral contraceptives as well. For example, with respect to Lunabell tablets (tablets having the same ingredients and formulation as Ortho M-21 tablets that have been used as an oral contraceptive), adverse side effects have been reported to occur at a high rate of 87.9%. Primary examples of adverse side effects include abnormal genital bleeding (59.1%), nausea (26.3%), headache (16.2%), oligomenorrhea (14.6%), upper abdominal pain (8.6%), breast discomfort (8.1%) and menorrhagia (7.1%), while thrombosis and anaphylactic symptoms have also been reported as serious adverse side effects (Non-Patent Document 6). In addition, low-dose oral contraceptives have also been reported to increase the risk of the onset or exacerbation of estrogen-dependent malignant tumors (Non-Patent Document 6). Moreover, due to their inhibitory action on ovulation, they are unsuitable for use by women desiring to bear children since it is not possible to become pregnant while continuing to take these drugs (Non-Patent Documents 6 and 7).

Tranilast is a drug that has been conventionally used for the treatment and/or prevention of mainly bronchial asthma and allergic rhinitis based on its action of inhibiting the release of chemical mediators. In addition, in addition to its inhibitory action on the release of chemical mediators, tranilast also has an action that inhibits collagen synthesis, and is known to have therapeutic effects against diseases involving excessive proliferation of vascular endothelial cells such as restenosis following PTCA, cardiac hypertrophy, atherosclerosis, angiogenesis inhibition, coronary hypertrophy following heart transplant, hypertensive arteriolopathy and heart failure (see Patent Documents 1 to 8). However, tranilast, derivatives thereof or salts thereof are not known to be effective as a prophylactic and/or therapeutic agent for dysmenorrhea and/or associated symptoms thereof, and there have also been no findings suggesting such.

Patent Document 1: Japanese Patent Laid-open Publication No. H5-163222
Patent Document 2: Japanese Patent Laid-open Publication No. H6-135829
Patent Document 3: Japanese Patent Laid-open Publication No. H7-277966
Patent Document 4: Japanese Patent Laid-open Publication No. H9-227371
Patent Document 5: WO 97/29744
Patent Document 6: WO 01/05394
Patent Document 7: WO 01/13911
Patent Document 8: WO 01/13952
Non-Patent Document 1: Modern Physician, Vol. 29, No. 3, p. 399, 2009
Non-Patent Document 2: International Statistical Classification of Diseases and Related Health Problems, 10th Revision Version for 2007, Chapter XIV: Diseases of the Genitourinary System
Non-Patent Document 3: Voltaren Tablets, Interview Form, Revised June 2005 Edition (Revised 9th Edition), p. 11
Non-Patent Document 4: Ibuprofen Tablets/Ibuprofen Powder, Interview Form, Revised January 2010 Edition (13th Edition)
Non-Patent Document 5: Naproxen Tablets/Naproxen Capsules, Interview Form, Revised October 2009 Edition (11th Edition)
Non-Patent Document 6: Lunabell, Interview Form, Revised January 2010 Edition (New Form 4th Edition), p. 30, 31, 9
Non-Patent Document 7: Nuttall I.D., et al., Contraception, 1982; 25: 463-469

SUMMARY OF THE INVENTION

An object of the present invention is to provide a prophylactic and/or therapeutic agent for dysmenorrhea and/or associated symptoms thereof.

Based on the approach that some form of abnormality is present in the endometrial tissue of patients with respect to determining the mechanism of occurrence of dysmenorrhea, the inventors of the present invention conducted detailed examinations of specimen tissues of dysmenorrhea patients using immunohistochemical techniques. As a result, it was found that an abnormality is observed in changes in the morphology of the endometrial tissue of dysmenorrhea patients. Namely, although the endometrial epithelial tissue of healthy subjects (non-dysmenorrhea subjects) inherently undergoes a change from a mesenchymal form to an epithelial form during a transition period from a low basal temperature phase to a high-temperature phase prior to ovulation, in dysmenorrhea patients, findings were obtained indicating that this morphological change is delayed, with a prominent mesenchymal form continuing to be maintained even after entering the high-temperature phase (Example A). Since abnormalities of this morphological change in endometrial epithelial tissue in these patients are suggested to be related to disease, the inventors of the present invention further conducted a search for drugs that normalize this morphological change, or in other words, cause endometrial epithelial tissue to change from a mesenchymal form to an epithelial form. As a result, it was newly discovered that tranilast has an action that induces the mesenchymal form of endometrial epithelial cells to the epithelial form (Examples B1 and B2).

Although these results suggest that tranilast is effective for the treatment of dysmenorrhea, at the time of the demonstration thereof, since 1) menstruation per se is a physiological phenomenon that is only observed in certain primates (Journal of Mammalian Ova Research, Vol. 23, p. 163, 2006), thereby making model evaluation difficult due to the absence of animal models such as rodent models, the use of which has been recognized in this field, including related diseases, and 2) tranilast is a drug that is already applied clinically for other diseases and for which the safety thereof has been verified, the effects thereof were demonstrated by obtaining the approval of the ethics committee at a clinical institution along with the informed consent of patients, and then administering tranilast to multiple actual dysmenorrhea patients for a predetermined period of time. As a result, tranilast was confirmed to clearly demonstrate ameliorative effects on dysmenorrhea in both patients presenting with functional (primary) dysmenorrhea and organic (secondary) dysmenorrhea following administration thereof.

On the basis of these results, the inventors of the present invention found that tranilast is effective as a prophylactic and/or therapeutic agent for dysmenorrhea and/or associated symptoms thereof, thereby leading to completion of the present invention.

Namely, the following are provided by the present invention.

(1) A pharmaceutical composition for the prevention and/or treatment of dysmenorrhea and/or associated symptoms thereof, comprising, as an active ingredient thereof, tranilast, a derivative thereof or a salt thereof (2) The pharmaceutical composition described in (1) above, wherein the associated symptoms are at least one symptom selected from the group consisting of lower abdominal distension, nausea and vomiting, headache, diarrhea, lethargy, loss of appetite, restlessness, lower back pain, lower extremity pain, anemia, menorrhagia and malaise.

(3) The pharmaceutical composition described in (1) or (2) above, which is a pharmaceutical composition for the prevention and/or treatment of functional (primary) dysmenorrhea.

(4) The pharmaceutical composition described in (1) or (2) above, which is a pharmaceutical composition for the prevention and/or treatment of organic (secondary) dysmenorrhea.

(5) Tranilast, a derivative thereof or a salt thereof for the prevention and/or treatment of dysmenorrhea and/or associated symptoms thereof (6) A kit comprising tranilast, a derivative thereof or a salt thereof for the prevention and/or treatment of dysmenorrhea and/or associated symptoms thereof (7) Use of tranilast in the manufacture of a medicament for the prevention and/or treatment of dysmenorrhea and/or associated symptoms thereof (8) A method for the prevention and/or treatment of dysmenorrhea and/or associated symptoms thereof, comprising a step for administrating tranilast, a derivative thereof or a salt thereof to a patient in need of thereof (9) A method for the prevention and/or treatment of dysmenorrhea and/or associated symptoms thereof, comprising daily administration of 50 mg to 1000 mg per day of tranilast, a derivative thereof or a salt thereof by oral administration three times a day to a patient in need thereof.

The tranilast, derivative thereof or salt thereof of the present invention is able to alleviate dysmenorrhea and/or associated symptoms thereof, and can therefore be used as a prophylactic and/or therapeutic agent for dysmenorrhea and/or associated symptoms thereof. In addition, administration of tranilast, a derivative thereof or a salt thereof allows the obtaining of adequate effects even if administered alone, without causing adverse side effects observed accompanying administration of conventional analgesics, herbal medicines and low-dose oral contraceptives, while also being effective when combined with these existing therapeutic agents such as low-dose oral contraceptives or hormone preparations. In addition, as the condition of a patient continues to improve as a result of taking tranilast, a derivative thereof or a salt thereof, the dosage of analgesics taken concomitantly as needed can be reduced considerably.

BRIEF DESCRIPTION OF THE DRAWINGS

The application file contains at least one drawing executed in color. Copies of this patent application publication with color drawing(s) will be provided by the Office upon request and payment of the necessary fee.

FIG. 8A is a bar graph showing the alleviating effects of tranilast on lower abdominal pain and lower back pain associated with dysmenorrhea during menstruation obtained from a clinical study of tranilast administration conducted on subjects A, B, C, D, E, F and G. Average values of pain scores during the menstrual period at the start of administration in each subject are shown on the left side of the graph, while average values of pain scores during the final menstrual period during the administration period are shown on the right side of the graph. NRS scores representing pain intensity are plotted on the vertical axis, and a higher bar indicates greater intensity of pain.

FIG. 8B is a table indicating degrees of improvement in the average values of pain scores of the final menstrual period during the administration period from the average values of pain scores during the menstrual period at the start of administration as shown in FIG. 8A. "Pain score improvement rate" was calculated with the formula {1-(NRS score during final menstrual period/NRS score during menstrual period at start of administration)}×100, and a larger value for pain score improvement rate indicates a higher degree of pain relief.

FIG. 10 is a table indicating findings obtained through interviews conducted by a gynecological specialist on subjects A, C, D, E, F and G. Furthermore, interview findings were not obtained from subject B since she was unable to regularly undergo a gynecological examination. The table shows interview findings pertaining to lower abdominal pain and lower back pain during menstruation obtained by a physician prior to the start of administration, and interview findings obtained in the same way by the physician at the time of the final visit during the administration period. "Bedridden" indicates that the patient was forced to lie down due to excessively intense pain despite having taken an analgesic, "analgesic" indicates that although the patient experienced pain, she was able to carry out daily activities by taking an analgesic, "bearable" indicates that although the patient experienced pain, the degree of pain was bearable and not require the use of an analgesic, and "--" indicates that there was no pain whatsoever or only slight pain was felt.

FIG. 11 is a table indicating findings obtained through interviews conducted by a gynecological specialist on a subject H in the same manner as in the case of FIG. 10.

MODES FOR CARRYING OUT THE INVENTION

Figure 1:
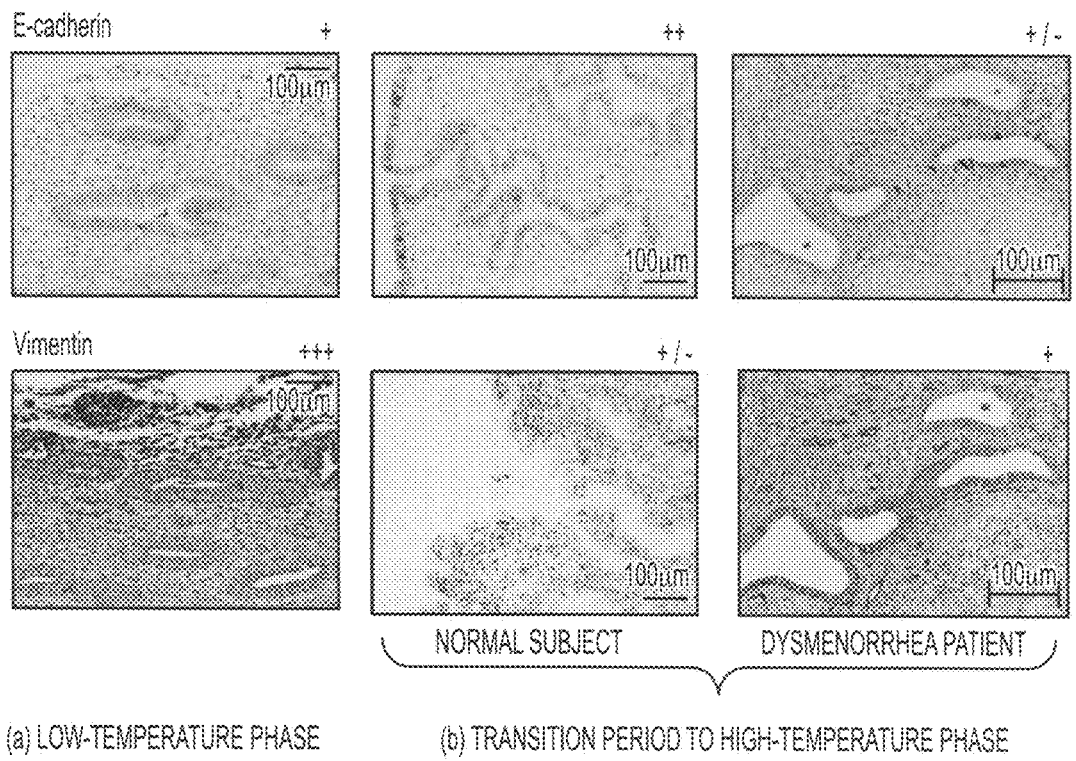
FIG. 1(a) is a drawing showing phase contrast micrographs of endometrial epithelial tissue sections in a low-temperature phase.
FIG. 1(b) is a drawing showing phase contrast micrographs of endometrial epithelial tissue sections in a transition period to a high-temperature phase. The morphological change to an epithelial form was found to be delayed in dysmenorrhea patients, while instead exhibiting a mesenchymal form.

1. Pharmaceutical Composition for Prevention and/or Treatment of Dysmenorrhea Containing Tranilast The present invention, in an embodiment thereof, provides a pharmaceutical composition (or drug) for the prevention and/or treatment of dysmenorrhea and/or associated symptoms thereof, comprising as an active ingredient thereof tranilast, a derivative thereof or a salt thereof. The pharmaceutical composition (or drug) of the present invention further contains a pharmaceutically acceptable carrier.

As used herein, "dysmenorrhea" refers to, among the symptoms associated with pain of a peripheral site centering on the pelvis, such as lower abdominal pain or lower back pain, occurring immediately before, during or immediately after menstruation, those that are associated with intense pain and require medical actions (namely, medical treatment). In addition, dysmenorrhea is classified as N94 according to the International Classifications of Disease ICD10, and is further classified as functional (primary) dysmenorrhea (N94.4) and organic (secondary) dysmenorrhea (N94.5).

In the present specification, "associated symptoms of dysmenorrhea" refer to various concomitant symptoms (such as headache, malaise or menorrhagia) that manifest in patients accompanying dysmenorrhea.

In the present specification, "prevention and/or treatment of dysmenorrhea and/or associated symptoms thereof" refers to the prevention and/or treatment of dysmenorrhea and/or the prevention and/or treatment of concomitant symptoms accompanying dysmenorrhea. "Treatment" includes not only definitive treatment but also cases in which a patient's condition improves as compared with that prior to treatment even though the treatment may not be a radical treatment (or in other words, "improvement of symptoms"). "Prevention" includes not only the performing of preventive measures in the case a disease is expected to occur in advance, but also measures performed on an individual in order to prevent recurrence of a disease that has previously been cured.

"Tranilast" (chemical name: N-(3,4-dimethoxycinnamoyl) anthranilic acid) is a compound having a molecular weight of 327.33 ($C_{18}H_{17}NO_5$) represented by the following structural formula:

[Compound 1]

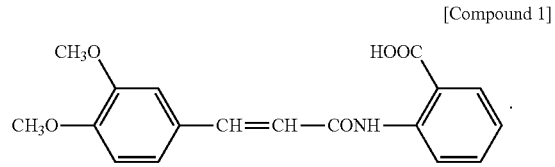

It is in the form of light yellow crystals or a crystalline powder, and is odorless and tasteless. It is freely soluble in N,N-dimethylformamide, soluble in 1,4-dioxane, slightly soluble in ethanol, very slightly soluble in diethyl ether, and practically insoluble in water. Blood concentration at a normal dose demonstrates a Cmax of 12.6 μm/mL (after 2 hours) following single-dose administration at 100 mg (normal adult), and demonstrates a Cmax of 2.2 μg/mL (after 36 hours to 66 hours) following continuous infusion for 3.5 days at 7.5 mg/kg (normal adult) (refer to "Pharmaceutical Interview Form", new form, 2nd edition, p. 19, July 2006, by Product information department of Kissei Pharmaceutical Co., Ltd. (the entire disclosure of which is incorporated herein by reference)).

Although the pharmaceutical composition of the present invention contains tranilast as an active ingredient thereof, that active ingredient is not limited to tranilast per se, but rather may also be a salt of tranilast, a derivative of tranilast or a salt of a derivative of tranilast having activity equal to that of tranilast.

"Activity equal to that of tranilast" includes activity that demonstrates a preventive and/or therapeutic effect (e.g., reduction of pain) against dysmenorrhea and/or associated symptoms thereof as indicated in examples of the present specification (an example of such an activity is an action that promotes a morphological change in cells from a mesenchymal form to an epithelial form). This preventive and/or therapeutic effect can be easily evaluated by a person with ordinary skill in the art in accordance with procedures indicated in examples of the specification of the present application. In addition, the action of promoting a morphological change in cells from a mesenchymal form to an epithelial form can be easily confirmed by a person with ordinary skill in the art by microscopically observing morphological changes in cells during addition of a target compound to cultured cells as described in examples of the present specification.

Examples of "derivatives of tranilast" include various tranilast derivatives described in Japanese Patent Application Laid-open No. S49-93335, U.S. Pat. No. 3,940,422 (Specification) and WO 01/25190 A1 (these publications are cited in their entirety in the present specification as references). More specifically, examples of tranilast derivatives include an aromatic carboxylic acid amide derivative represented by the following general formula:

[Compound 2]

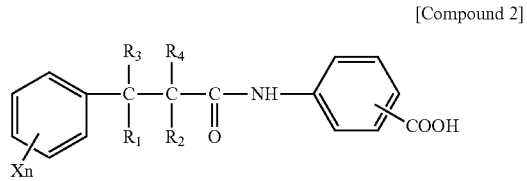

(wherein, $R_1$ and $R_2$ respectively represent a hydrogen atom or alkyl group having 1 to 4 carbon atoms, $R_3$ and $R_4$ respectively represent a hydrogen atom or both form a chemical bond, X represents a hydroxyl group, halogen atom, alkyl group having 1 to 4 carbon atoms or alkoxy group having 1 to 4 carbon atoms, n represents an integer of 1 to 3, and in the case X represents two alkyl groups or alkoxy groups, both groups may bond to form a ring).

The phrase "pharmaceutically acceptable" is used in the present specification to indicate a compound, material, composition and/or drug form that has a rational benefit/risk ratio within the range of an ordinary medical evaluation, does not exhibit excessive toxicity, irritation, allergic reactions or other problems or complications, and is suitable for use by allowing to contact human and animal tissue.

Tranilast, a derivative thereof or a salt thereof can be used as a prophylactic agent and/or therapeutic agent for dysmenorrhea and/or associated symptoms thereof 2. Preparation, Formulation and Administration of Prophylactic and/or Therapeutic Agent of the Present Invention The prophylactic and/or therapeutic agent for dysmenorrhea and/or associated symptoms thereof used in the present invention can be produced by mixing tranilast, a derivative thereof or a salt thereof with a commonly used preparation carrier.

The preparation carrier may be used by suitably combining with tranilast depending on the mode of administration. Examples of such a preparation carrier include vehicles such as lactose, lubricants such as magnesium stearate, disintegrating agents such as carboxy methyl cellulose, binders such as hydroxypropyl methyl cellulose, surfactants such as Macrogol, effervescent agents such as sodium bicarbonate, dissolving assistants such as cyclodextrin, souring agents such as citric acid, stabilizers such as sodium edetate and pH adjusters such as phosphates.

For administration of tranilast, derivative thereof of salt thereof used in the present invention together with another concomitant agent, an internally taken solid preparation or an internally taken liquid preparation for oral administration can be used, or an injection preparation, externally applied preparation, suppository, eye drops or inhalant and the like for parenteral administration can be used.

Examples of internally taken solid preparations for oral administration include tablets, pills, capsules, powders and granules. Capsules include hard capsules and soft capsules. In addition, tablets include sublingual tablets, buccal tablets and rapidly disintegrating buccal tablets.

In such internally taken solid preparations, one or more active substances are either used as or are formulated in accordance with ordinary methods by mixing with a vehicle (such as lactose, mannitol, glucose, microcrystalline cellulose or starch), binder (such as hydroxypropyl cellulose, polyvinylpyrrolidone or magnesium aluminate metasilicate), disintegrating agent (such as fibrin calcium glycolate), lubricant (such as magnesium stearate), stabilizer or dissolving assistant (such as glutamic acid or aspartic acid). In addition, as necessary, internally taken solid preparations may also be coated with a coating agent (such as saccharose, gelatin, hydroxypropyl cellulose or hydroxypropyl methyl cellulose phthalate), or may be coated with two or more layers thereof. Moreover, capsules made of absorbable substances in the manner of gelatin are also included.

The sublingual tablets, buccal tablets and rapidly disintegrating buccal tablets used in the present invention are produced and prepared in compliance with known methods.

Examples of internally taken liquids for oral administration include pharmaceutically acceptable aqueous solutions, suspensions, emulsions, syrups and elixirs. In these liquid agents, one or more active substances are dissolved, suspended or emulsified in a commonly used diluent (such as purified water, ethanol or a mixed liquid thereof). Moreover, these liquid agents may contain a wetting agent, suspending agent, emulsifier, sweetener, flavoring agent, aromatic, preservative or buffer and the like.

Examples of drug forms of externally applied preparations for parenteral administration include ointments, gels, creams, poultices, patches, liniments, aerosols, inhalants, sprays, eye drops and nose drops. These contain one or more active substances and are produced and prepared according to known methods or normally used formulations.

Examples of injection preparations for parenteral administration include solid injection preparations used in the form dissolved or suspended in a solution, suspension, emulsion or a solvent before use. Injection preparations are used in the form dissolved, suspended or emulsified with one or more active substances in a solvent. Examples of solvents used include distilled water for injection, physiological saline, vegetable oil, alcohols such as propylene glycol, polyethylene glycol or ethanol, and combinations thereof. Moreover, these injection preparations may also contain a stabilizer, dissolving assistant (such as glutamic acid, aspartic acid or Polysorbate 80®), suspending agent, emulsifier, analgesic, buffer or preservative and the like. These injection preparations are produced and prepared by an aseptic or sterile procedure in the final step. In addition, these injection preparations can also be produced in a sterile solid preparation such as a freeze-dried preparation, and then dissolved in sterilized or sterile distilled water for injection or other solvent prior to use.

Examples of other compositions for parenteral administration those containing one or more active substances such as suppositories for intrarectal administration or pessaries for intravaginal administration formulated according to ordinary methods.

A chemical mediator release inhibitor contained in the above-mentioned preparations is suitably determined and prepared in each drug. In the case of tranilast, for example, it is contained within the range of 50 mg to 1000 mg, preferably within the range of 100 mg to 1000 mg and most preferably within the range of 100 mg to 500 mg per day for oral administration to adults, or within the range of 10 mg to 1000 mg, preferably within the range of 30 mg to 500 mg and most preferably within the range of 50 mg to 400 mg per day for parenteral administration to adults. Naturally, since dosage varies according to various conditions, the chemical mediator release inhibitor may be adequate at dosages lower than the above-mentioned dosages or may be required to be administered at a dosage that exceeds the above-mentioned ranges.

Although tranilast, a derivative thereof or a salt thereof may be administered by itself to demonstrate its meritorious effects, by administering together with a known analgesic, herbal medicine or low-dose oral contraceptive, the dosage of the analgesic, herbal medicine or low-dose oral contraceptive can be reduced considerably.

Although the following provides a more detailed explanation of the present invention based on examples thereof, the present invention is not limited to these examples.

EXAMPLES

Example A

Analysis of Morphological Changes in Endometrial Epithelial Tissue of Dysmenorrhea Patients by Immunostaining (Method)

Paraffin was removed from paraffin sections of endometrial epithelial tissue of non-dysmenorrhea patients and dysmenorrhea patients followed by subjecting to hydrophilic treatment with ethanol and activation treatment by subjecting to two rounds of heat treatment with citrate buffer (pH 6.0) for 5 minutes each. Subsequently, after blocking for 20 minutes at room temperature using 3% BSA/PBS, primary antibodies consisting of E-cadherin antibody (Monoclonal Mouse Anti-Human E-cadherin Clone NCH-38, Dako) and anti-vimentin antibody (Monoclonal Mouse Anti-Vimentin Clone V9, Dako) were both allowed to react after diluting 200-fold with 1.5% BSA/PBS.

After incubating for 1 day at 4° C., mouse secondary antibody (M.O.M. Biotinylated Anti-Mouse Ig-G Reagent, Vector) was allowed to react for 30 minutes at room temperature after diluting 200-fold with 1.5% BSA/PBS followed by staining with DAB (ImmPACT DAB, Vector). The stained samples were subjected to dehydration treatment followed by sealing and then photographed using a phase contrast microscope (Olympus BX51).

(Results)

FIG. 1 shows phase contrast micrographs of endometrial epithelial tissue sections in a low-temperature phase (a) and a high-temperature phase transition period (b) as captured in the manner described above. Although the endometrial tissue exhibiting a mesenchymal form in the low-temperature phase converts to an epithelial form during a transition period to a high-temperature phase in normal subjects, in dysmenorrhea patients, the morphological change to the epithelial form was found to be delayed and the endometrial tissue maintained a mesenchymal form.

Example B1

Action of Tranilast (Action of Causing Transition of Cell Morphology from Mesenchymal Form to Epithelial Form)

(Method)

Immortalized human retinal pigment epithelial cell line ARPE-19 (ATCC No.: CRL-2302) was disseminated into a 96-well glass plate (EZView Culture Plate, LB Cover Glass Bottom, 96 wells, Iwaki) at $1\times10^4$ cells/well followed by culturing at 37° C. in a 5% $CO_2$ environment. After 5 days, 150 µl aliquots each of DMEM-F12 (serum-free, Sigma-Aldrich) medium supplemented by 5 ng/ml of TGFβ2 and 100 ng/ml of TNFα were prepared and used to replace the original medium in the wells and cultured at 37° C. in a 5% $CO_2$ environment.

After 48 hours, the plate was removed from the incubator followed by the addition of tranilast (1 µg/ml) and culturing at 37° C. in a 5% $CO_2$ environment. After 96 hours, the plate was washed with PBS and the cells were fixed for 30 minutes with 4% paraformaldehyde (Wako), and after washing with PBS, were stained for 1 hour with F-actin (Alexa Fluor 568 Phalloidin, Invitrogen) and nuclei (Hoechst 33342, Invitrogen) followed by washing with PBS and then immediately photographing using a fluorescence microscope (Keyence) at a magnification factor of 40×.

(Results)

Figure 2:
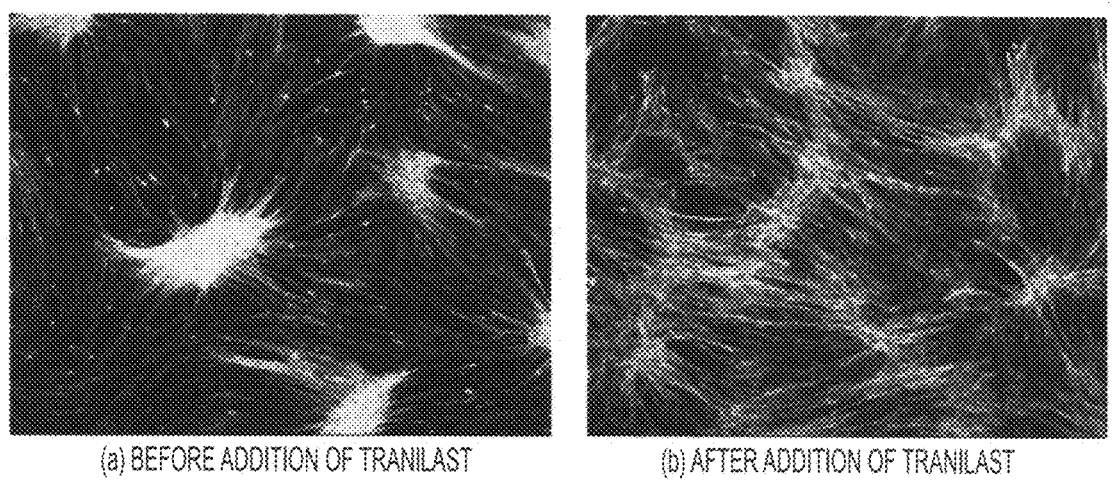
FIG. 2(a) shows the morphology of cultured cells prior to addition of tranilast after having allowed 48 hours to elapse from the time of addition of TGFβ2 and TNFα. The cells demonstrated a mesenchymal form, acquired motility, secreted an intercellular matrix and formed foci as a result of addition of TGFβ2 and TNFα.
FIG. 2(b) shows the morphology of cultured cells 96 hours after the addition of tranilast in FIG. 2(a). The formed foci were alleviated and the cells exhibited an epithelial form due to addition of tranilast.

FIG. 2(a) shows morphology of cultured cells at 48 hours after addition of TGFβ2 and TNFα but prior to addition of tranilast. FIG. 2(b) shows subsequent morphology of cultured cells at 96 hours after the addition of tranilast. Although the cells demonstrated a mesenchymal form, acquired motility, secreted an intercellular matrix and formed foci following addition of TGFβ2 and TNFα (FIG. 2(a)), the formed foci were found to be alleviated and the cells exhibited an epithelial form as a result of addition of tranilast (FIG. 2(b)).

Example B2

Action of Tranilast on Endometrial Epithelial Cells (Method)

Cell line EM-E6/E7/hTERT cells (EM) derived from endometrial epithelium were disseminated in a 6-well glass plate (EZView Culture Plate, LB Cover Glass Bottom, 6 wells, Iwaki) at $1\times10^5$ cells/well, followed by culturing for 2 days at 37° C. in an environment having a carbon dioxide concentration of 5% in DMEM/F12 medium and in the presence of 10% serum, and then culturing for 3 days after replacing the medium with serum-free DMEM/F12 medium.

Subsequently, tranilast (320 µM, 80 µM, 20 µM) was added to medium containing TGFβ2 at 5 ng/ml, TNFα at 100 ng/ml or both followed by replacing the medium. Protein was recovered 48 hours after having replaced the medium with the medium containing TGFβ2 or TNFα, and expression levels of fibronectin and N-cadherin were compared by western blotting.

Anti-fibronectin antibody (clone ID: F14, Epitomics) and anti-N-cadherin antibody (clone ID: 32/N-cadherin, BD Transduction Laboratories) were used for the antibodies.

(Results)

Figure 3:
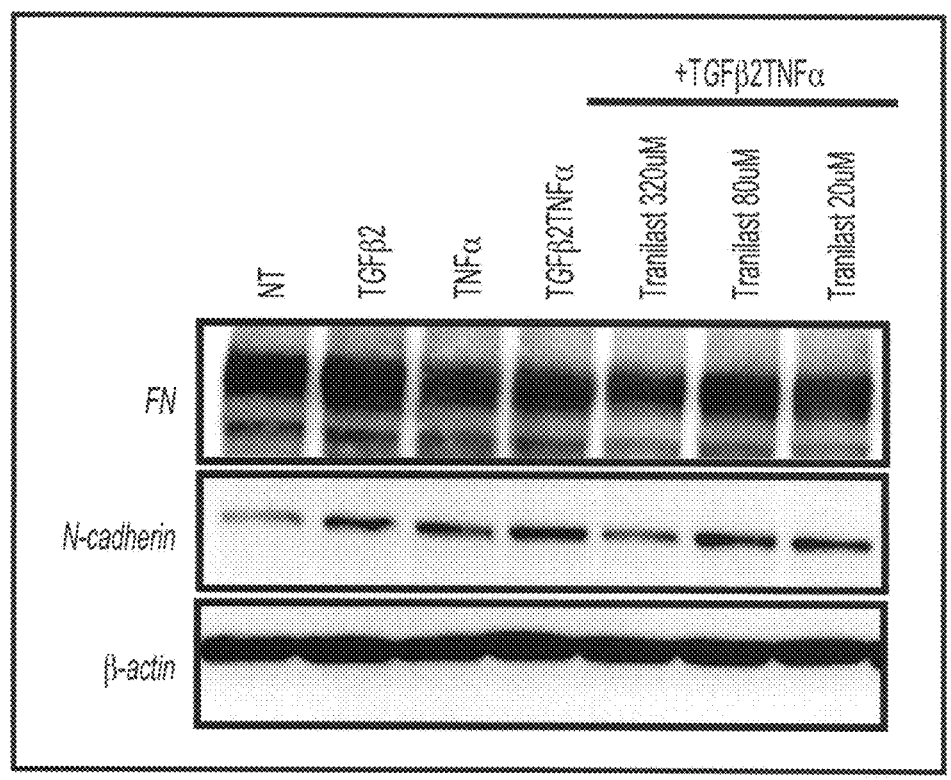
FIG. 3 shows the results of analyzing by western blotting changes in expression levels of the intercellular matrix molecule, fibronectin (FN) and the adhesive molecule, N-cadherin, for which increased expression is observed in mesenchymal cells, during culturing of a cell line (EM-E6/E7/hTERT cells) derived from endometrial epithelium following addition of TGFβ2, TNFα and tranilast with both TGFβ2 and TNFα.

FIG. 3 shows the results of analyzing by western blotting as described above.

On the basis of FIG. 3, it was determined that, although increases in fibronectin and N-cadherin, which is one of the characteristics of mesenchymal cells, were observed due to addition of TGFβ2 or TNFα (and the cells retained their mesenchymal form), the addition of tranilast inhibited the expression of these molecules (and the cells retained epithelial properties).

Example 1

Clinical Study of Therapeutic Effect of Oral Administration of Tranilast (1)

Tranilast was orally administered to a Subject A suffering from dysmenorrhea to evaluate the preventive and/or therapeutic effects of tranilast on dysmenorrhea and/or associated symptoms thereof.

Background information on the Subject A is as indicated below.

Subject A was an unmarried woman in her late thirties suffering from organic dysmenorrhea.

Observed symptoms included intense lower abdominal pain and lower back pain during menstruation, and the patient had been taking low-dose oral contraceptive Ortho M-21 tablets, and loxoprofen, loxonin and etodolac, which are NSAIDs, since July 2005 until just prior to the study.

Subject A was given 100 mg of tranilast three times a day by oral administration (300 mg per day, divided three times daily) daily for about six months starting on Sep. 1, 2008.

Menstrual pain was measured according to a numerical rating scale (NRS). In the NRS, the patient was asked to evaluate and record the degree of pain by herself by judging the degree of pain according to 11 levels ranging from level 0 indicating the absence of pain to level 10 indicating maximum pain. Menstrual blood loss was evaluated according to 5 levels ranging from level 0 indicating the absence of blood loss up to level 4 as blood loss increased.

Figure 4A:
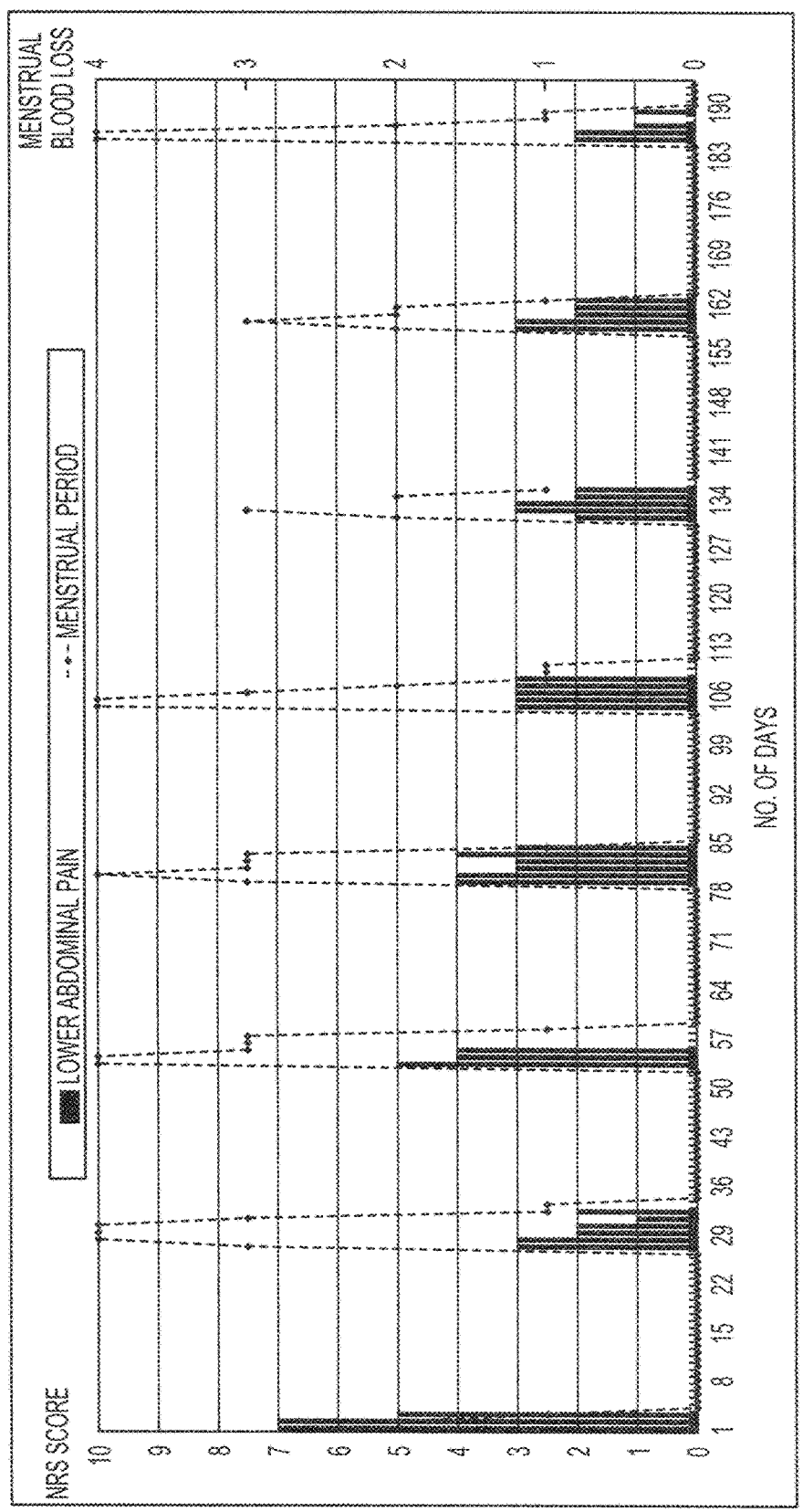
FIG. 4A is a graph showing the alleviating effects of tranilast on lower abdominal pain associated with dysmenorrhea during menstruation obtained from a clinical study of tranilast administration conducted on a subject A.
Figure 4B:
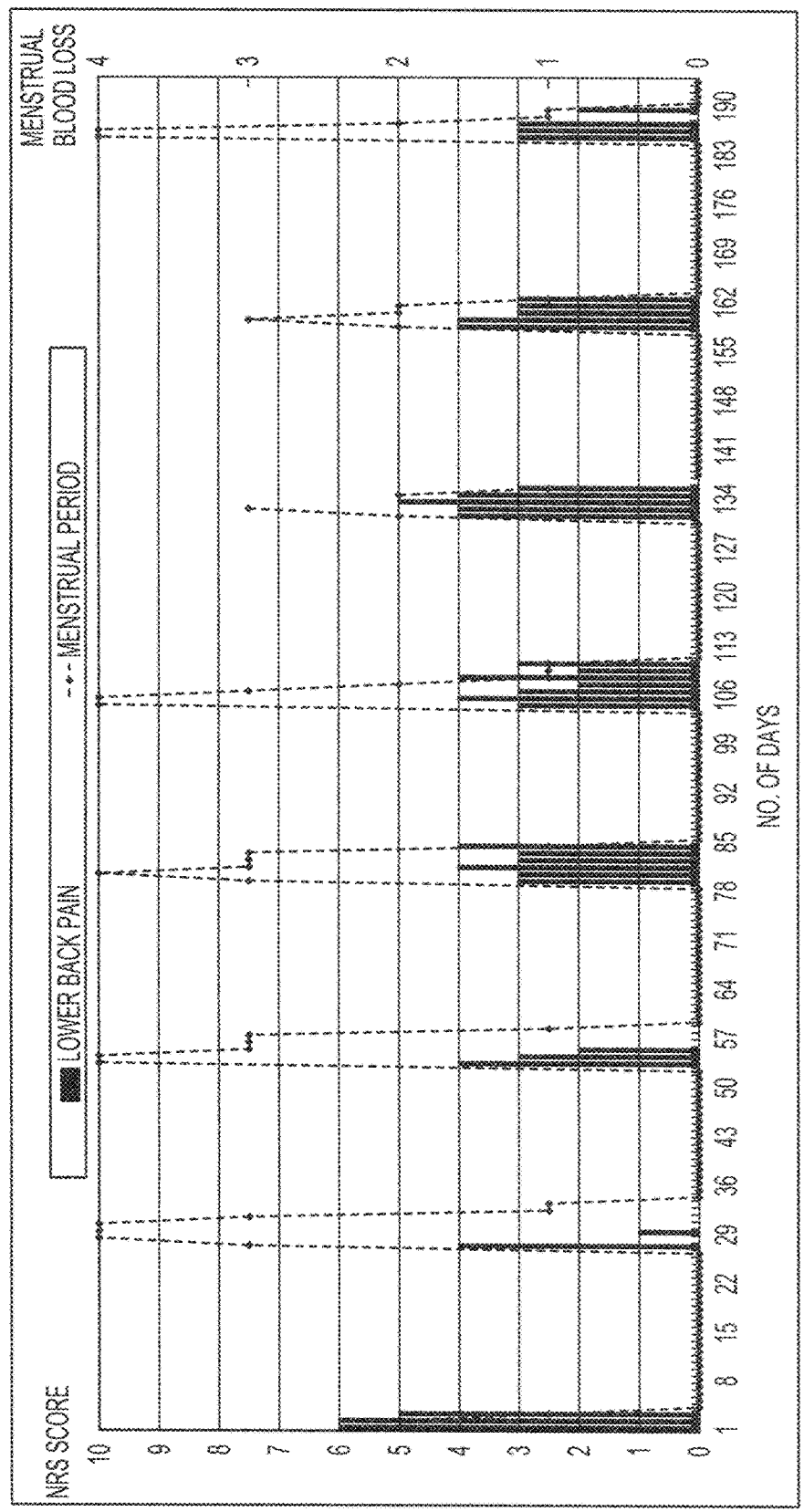
FIG. 4B is a graph showing the alleviating effects of tranilast on lower back pain associated with dysmenorrhea during menstruation obtained from a clinical study of tranilast administration conducted on a subject A.

FIGS. 4A and 4B indicate the results of evaluating lower abdominal pain and lower back pain during menstruation for Subject A. NRS scores for menstrual pain are plotted with a bar graph, while menstrual blood loss is plotted with a line graph. The number of days of administration (=evaluation period) is plotted on the horizontal axis, and covers a period of about six months from the start to completion of administration. Based on the bar graph, a trend of decrease in NRS scores with the number of days of administration of tranilast can be seen. Based on the line graph, a trend of decrease in menstrual blood loss with the number of days of administration can also be seen.

Figure 5A:
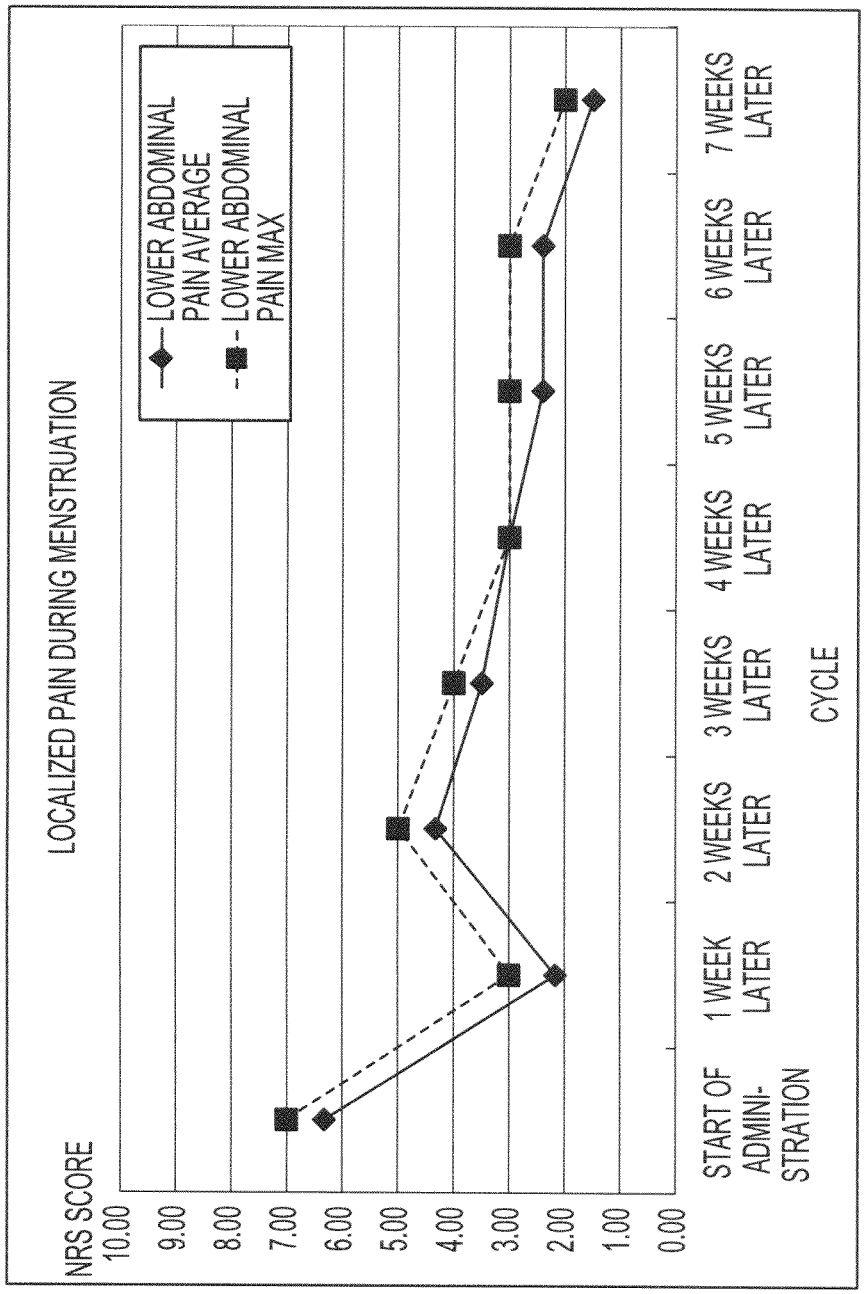
FIG. 5A is a graph showing the alleviating effects of tranilast on lower abdominal pain associated with dysmenorrhea during menstruation in a subject A similar to the results shown in FIG. 4A.
Figure 5B:
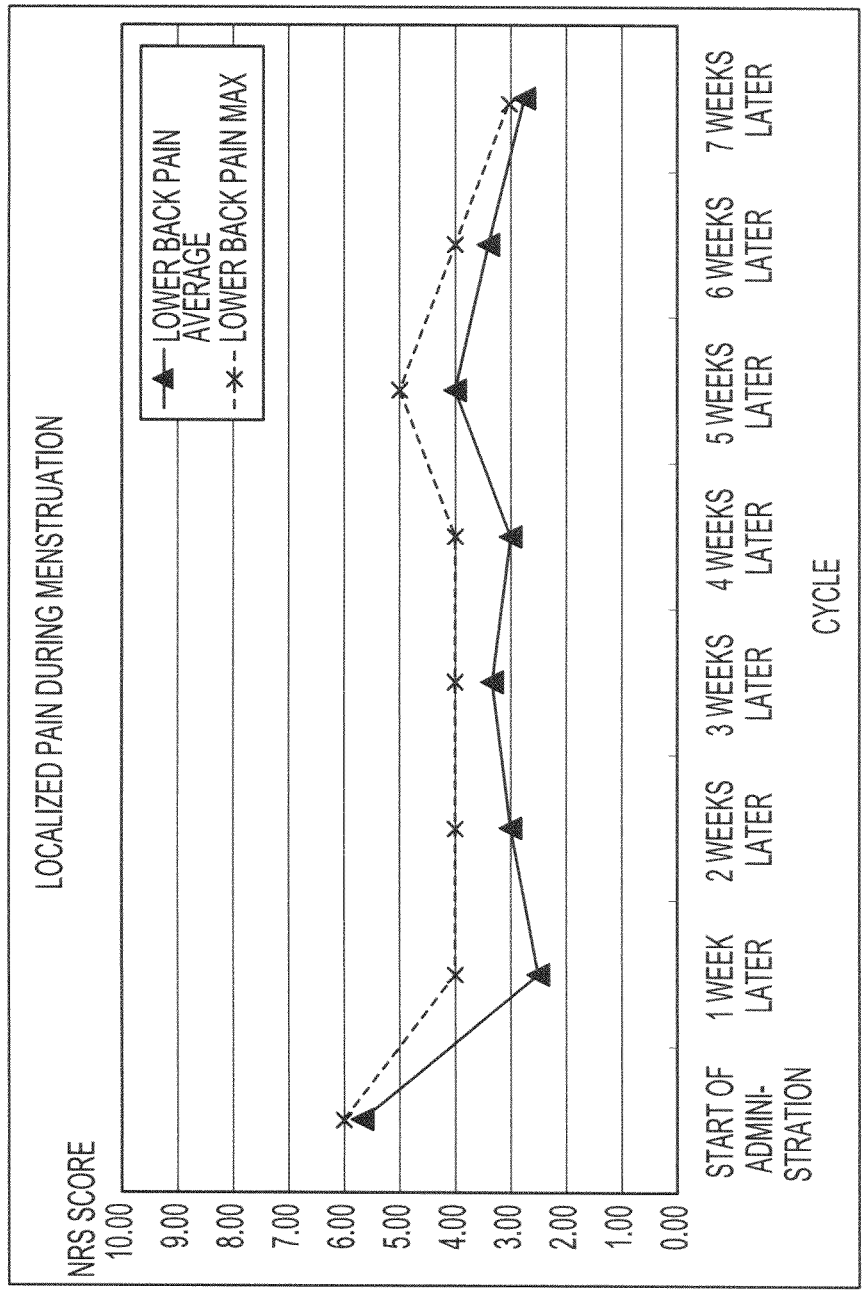
FIG. 5B is a graph showing the alleviating effects of tranilast on lower back pain associated with dysmenorrhea during menstruation in a subject A similar to the results shown in FIG. 4B.

FIGS. 5A and 5B show a bar graph in which the maximum values and average values of NRS scores for lower abdominal pain and lower back pain during each menstrual period obtained from the results of the evaluation of localized pain as described above are plotted for more ease of reading overall trends. Menstrual periods are plotted on the horizontal axis. In the case of Subject A, there were eight menstrual periods including that at the start of the study during the administration period of about six months.

The term "average" in the graphs indicates a value obtained by dividing the total sum of the pain level for each menstrual period by the number of days on which pain was felt.

The term "max" indicates a value of the day when the most intense pain was felt during each menstrual period.

On the basis of the above results, effects of alleviating lower abdominal pain and lower back pain were observed as a result of taking tranilast, and tranilast was determined to be useful as a prophylactic and/or therapeutic agent for dysmenorrhea and/or associated symptoms thereof.

Example 2

Clinical Study of Therapeutic Effect of Oral Administration of Tranilast (2)

Tranilast was orally administered to a Subject B suffering from dysmenorrhea to evaluate the preventive and/or therapeutic effects of tranilast on dysmenorrhea and/or associated symptoms thereof.

Background information on Subject B is as indicated below.

Subject B was a 45-year-old married woman suffering from functional dysmenorrhea.

[History]
Examined at a department of internal medicine in October 2006 and diagnosed with diabetes
Instructed to lose weight through dietary therapy and exercise therapy
Diabetes medication not prescribed, and examined once every two months (blood test)
[Menstrual Symptoms Before Started Taking Tranilast]
Tended to continue to exhibit menstrual irregularity.
Prolonged bleeding starting in March 2008, and accompanied by intense menstrual pain starting in April.
Had hardly ever taken an analgesic for menstrual pain prior to the study.
Examined and underwent testing at a department of gynecology on March 11, and recommended to undergo hormone therapy.
Examined on March 19. Underwent cancer examination and no abnormalities observed. Although recommended to undergo hormone therapy, since patient was unwilling to do so because of her previous experience of adverse side effects, decided to continue to monitor patient's progress.
Although took voltaren due to intense pain accompanying menstruation starting in April, caused gastric discomfort and made the patient feel poorly.
[Drugs Taken Before Start of Taking Tranilast]
Voltaren SR: 37.5 mg (taken when necessary for pain relief)
Adona (taken three times per day as hemostatic agent from April 8 to Apr. 21, 2008)
Tsumura 25: Keishibukuryogan (taken three times per day starting on Apr. 15, 2008 for treatment of menorrhagia).
[Symptoms After Start of Taking Tranilast]
Began oral administration of 100 mg of tranilast once per day (100 mg/day) starting on July 13.
Although less menstrual pain during August menstrual period, menstrual blood loss remained high.
Increased dosage of oral administration of 100 mg of tranilast to twice per day (200 mg/day, divided twice daily) starting on August 5.
Reduction of both pain and blood loss during September menstrual period.
Dosage of oral administration of 100 mg of tranilast returned to once per day (100 mg/day) starting on October 29.
Patient sensed both reduced pain and blood loss in December and tranilast determined to be effective.
There were no adverse side effects from taking tranilast.

Figure 6A:
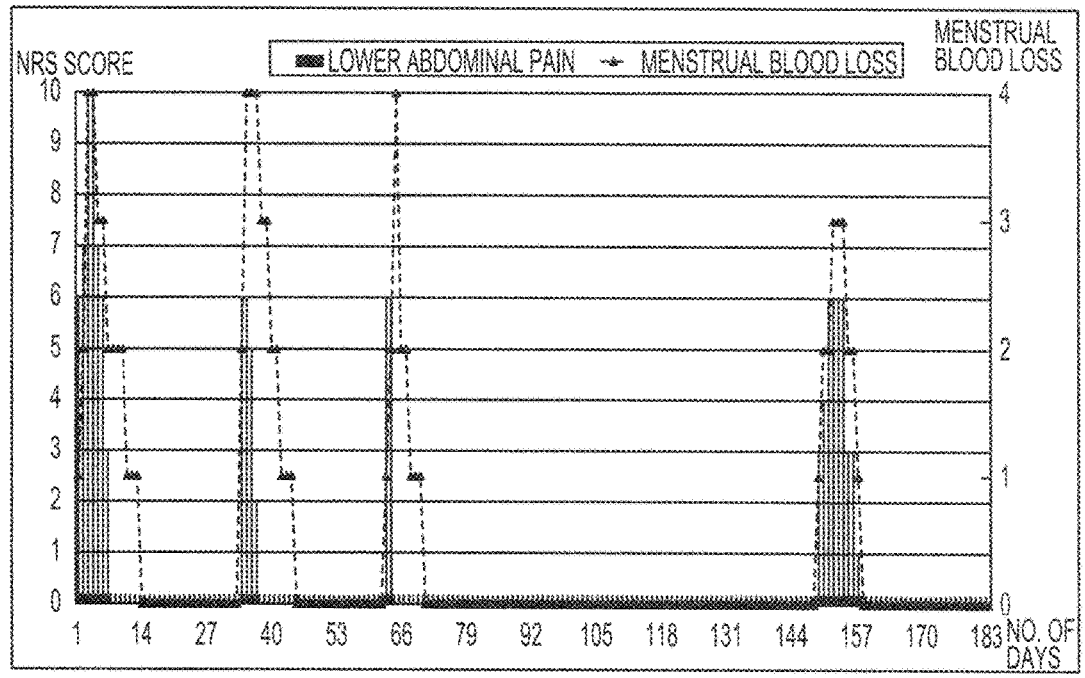
FIG. 6A is a graph showing the alleviating effects of tranilast on lower abdominal pain associated with dysmenorrhea during menstruation obtained from a clinical study of tranilast administration conducted on a subject B.
Figure 6B:
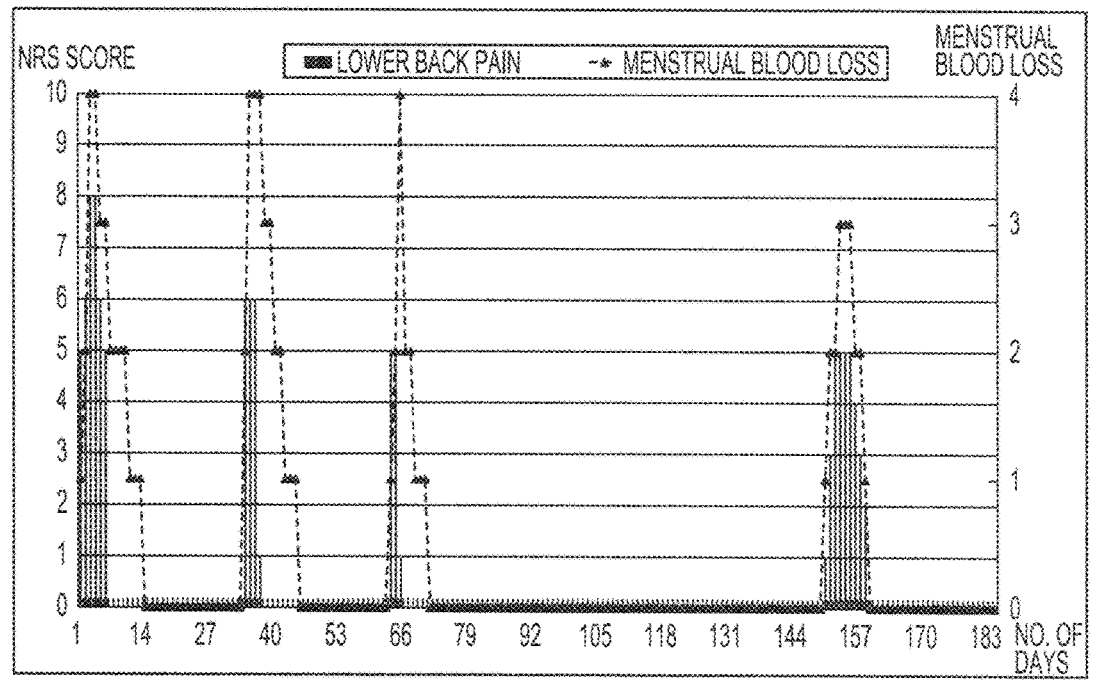
FIG. 6B is graph showing the alleviating effects of tranilast on lower back pain associated with dysmenorrhea during menstruation obtained from a clinical study of tranilast administration conducted on a subject B.

FIGS. 6A and 6B show the results of evaluating lower abdominal pain and lower back pain during menstruation for Subject B. NRS scores for menstrual pain are plotted with a bar graph, while menstrual blood loss is plotted with a line graph. The number of days of administration (=evaluation period) is plotted on the horizontal axis, and covers a period of about six months from the start to completion of administration. Based on both the bar graph and the line graph, pain and blood loss can be seen to clearly decrease following the start of administration of tranilast.

Figure 6C:
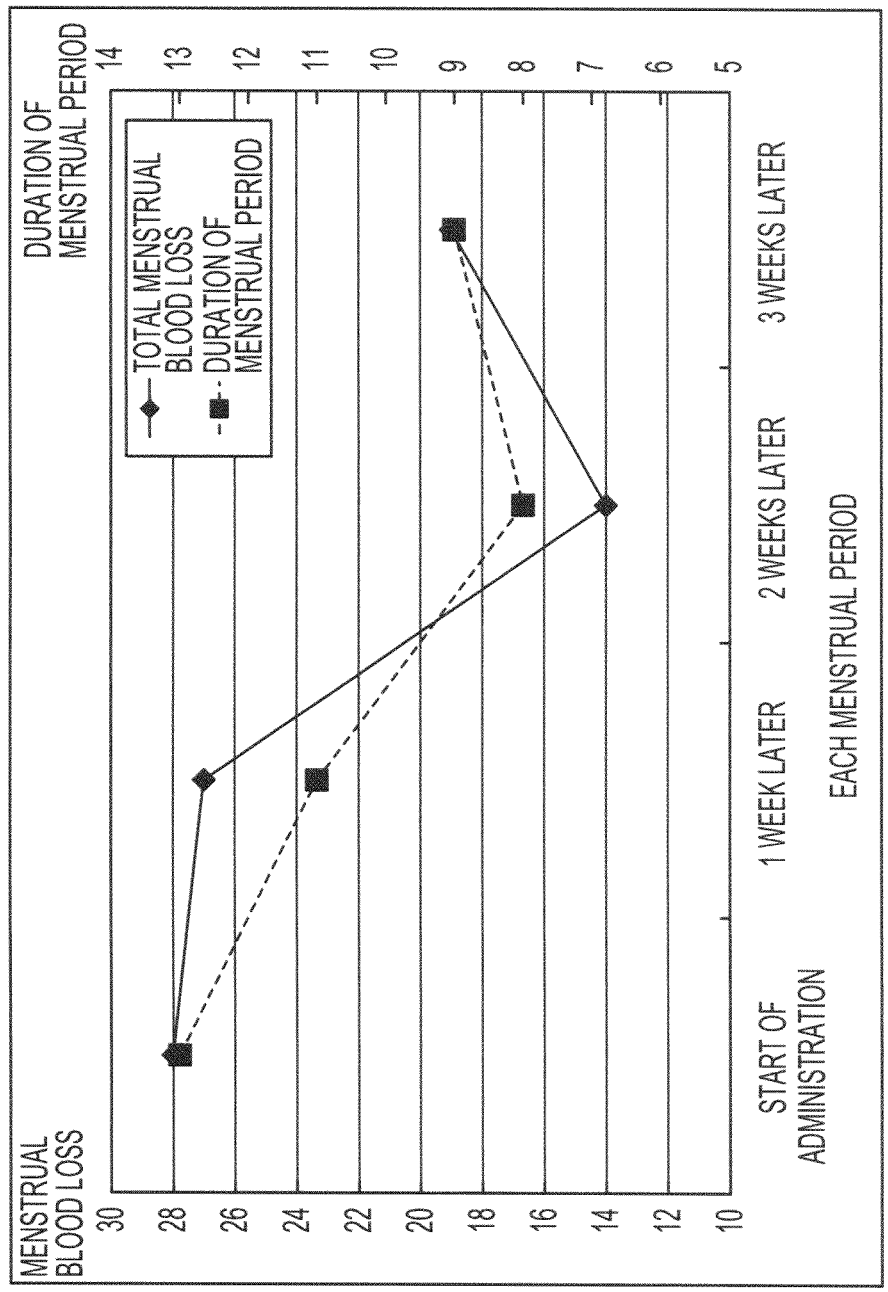
FIG. 6C is a graph showing the relationship between menstrual blood loss and the duration of menstruation during each menstrual period following commencement of administration of tranilast in a subject B.

FIG. 6C indicates changes in menstrual blood loss and the duration of menstruation in Subject B. Menstrual blood loss and the duration of menstruation decreased significantly following the start of administration of tranilast (Jul. 13, 2008), and symptoms of menorrhagia clearly improved.

Figure 7A:
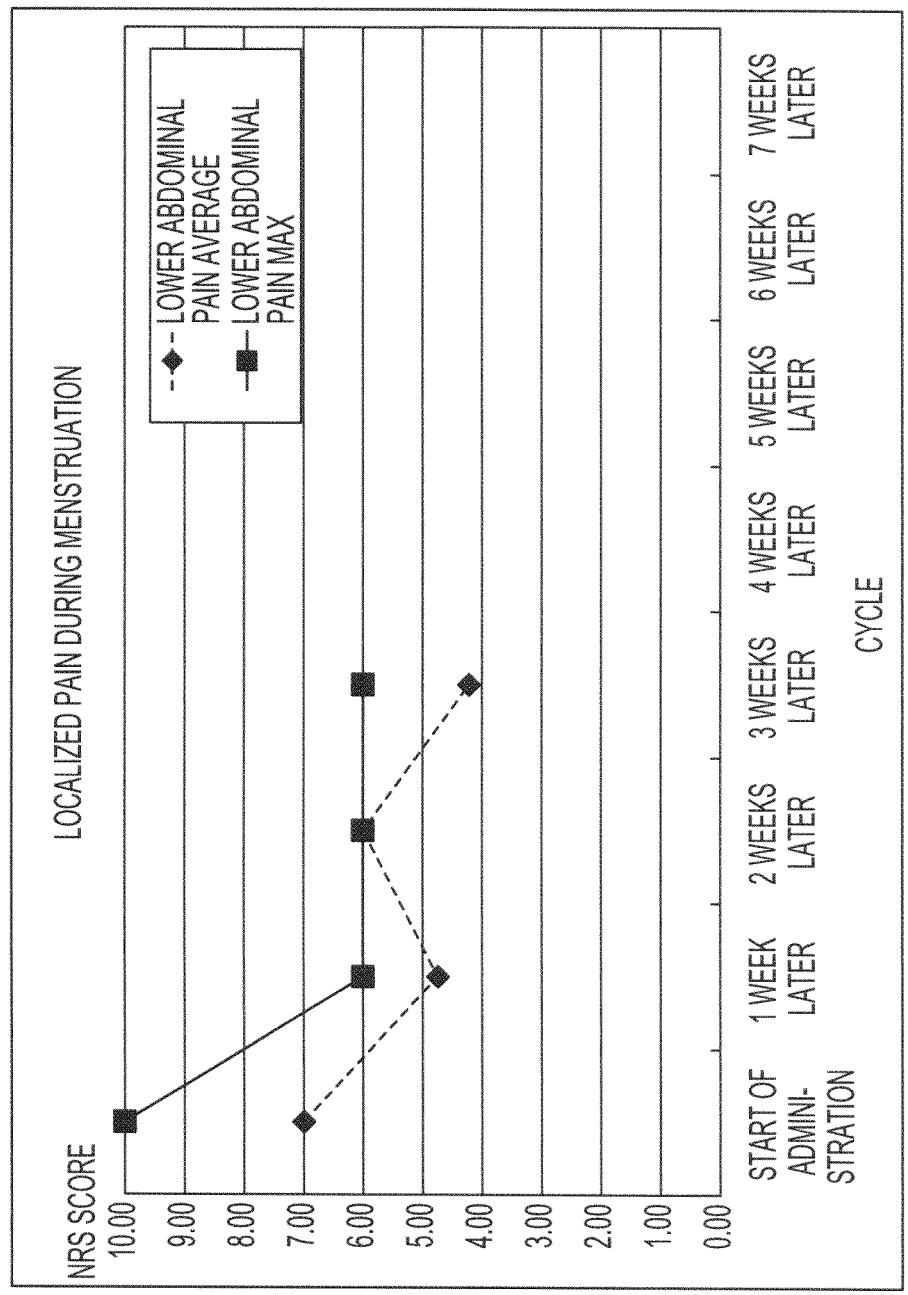
FIG. 7A is a graph showing the alleviating effects of tranilast on lower abdominal pain associated with dysmenorrhea during menstruation in a subject B similar to the results shown in FIG. 6A.
Figure 7B:
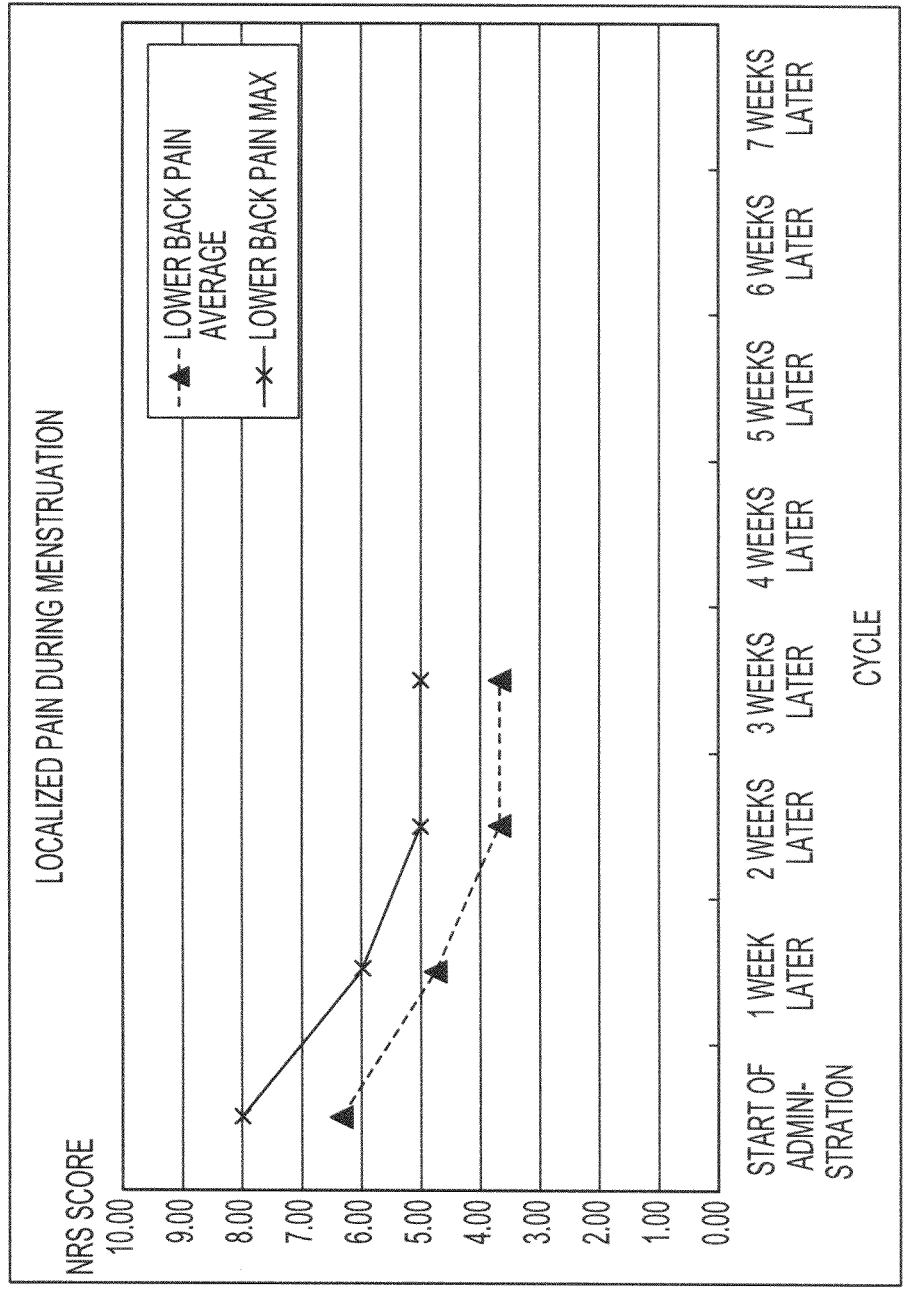
FIG. 7B is a graph showing the alleviating effects of tranilast on lower back pain associated with dysmenorrhea during menstruation in a subject B similar to the results shown in FIG. 6B.

FIGS. 7A and 7B show the results of plotting the maximum values and average values of NRS scores for lower abdominal pain and lower back pain during each menstrual period based on the results of the evaluation of localized pain shown in FIGS. 6A and 6B. Menstrual periods are plotted on the horizontal axis. In the case of Subject B, there were four menstrual periods, including that at the start of the study, during the administration period of about six months. The degree of localized pain during menstruation was determined to decrease significantly after beginning administration of tranilast.

Example 3

Clinical Study of Therapeutic Effect of Oral Administration of Tranilast (3)

Tranilast was orally administered to Subjects C, D, E, F and G suffering from dysmenorrhea to evaluate the preventive and/or therapeutic effects of tranilast on dysmenorrhea and/or associated symptoms thereof.

Pain during menstruation was evaluated by the record made for each day by the patient according the 11 levels from level 0 indicating the absence of pain to level 10 indicating maximum pain in the same manner as Subjects A and B, using the NRS method.

Figures 9A, 9B:
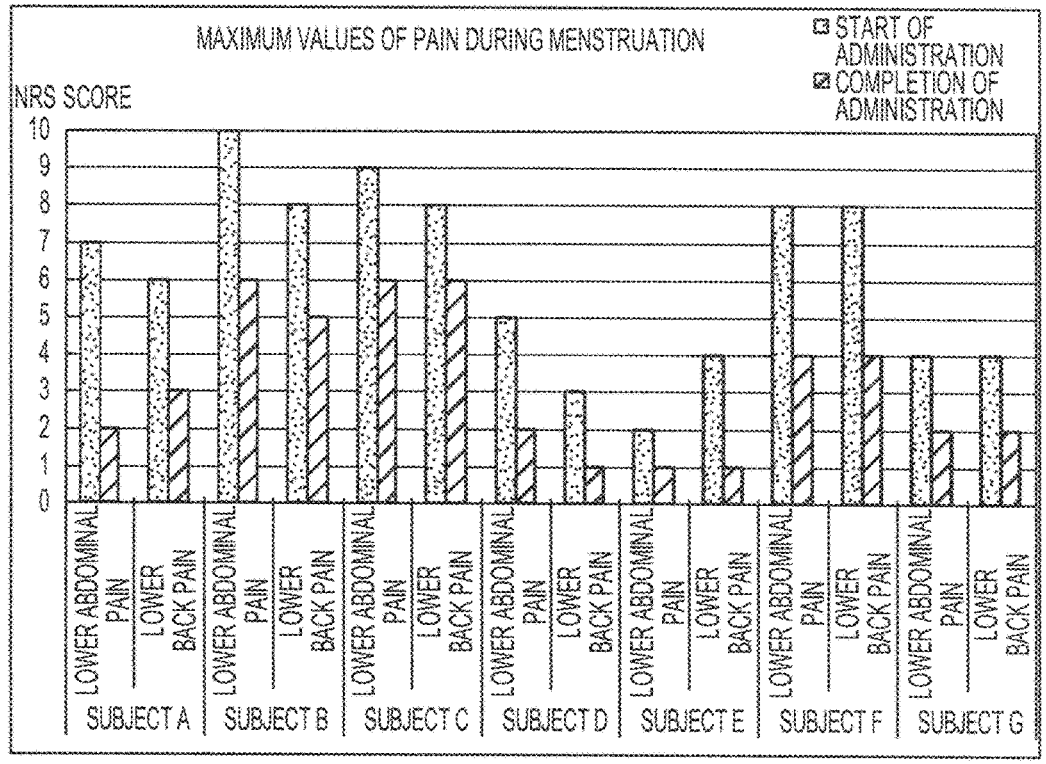
FIG. 9A is a bar graph showing the alleviating effects of tranilast on lower abdominal pain and lower back pain associated with dysmenorrhea in the same manner as FIG. 8A. The maximum values of pain scores during the menstrual period at the start of administration for each subject are shown on the left side of the graph, while the maximum values of pain scores during the final menstrual period during the administration period are shown on the right side of the graph. NRS scores representing pain intensity are plotted on the vertical axis, and a higher bar indicates greater intensity of pain.
FIG. 9B is a table indicating degrees of improvement in the maximum values of pain scores of the final menstrual period during the administration period from the maximum values of pain scores during the menstrual period at the start of administration as shown in FIG. 9A. A larger value for "pain score improvement rate" indicates a higher degree of pain relief.

The average values and maximum values of NRS scores indicating the intensity of pain during each menstrual period were derived, and the values were compared between the menstrual period at the start of administration and the last menstrual period during the administration period as shown in graphs of FIGS. 8A and 9A. In addition, the degrees of decrease in average values and maximum values for menstrual pain during the last menstrual period relative to the first menstrual period at the start of administration were represented as improvement rates, and are shown in FIGS. 8B and 9B.

As shown in FIGS. 8A and 8B and FIGS. 9A and 9B, each of the Subjects C, D, E, F and G, including Subjects A and B, exhibited prominent decreases in pain during menstruation during the last menstrual period of the administration period due to the effect of tranilast, as compared with that during the menstrual period at the start of administration.

Moreover, Subjects A, C, D, E, F and G, but excluding Subject B, underwent examinations at the facility conducting the clinical study at roughly one month intervals during the administration period, and were interviewed by a specialist in the department of gynecology. Interview findings before the start of administration and interview findings at the time of their final visit were compared and are shown in FIG. 10.

As shown in FIG. 10, interview findings were obtained from Subjects A, C, D, E and F that indicated that menstrual pain diminished at the time of their final visit during the administration period as compared with before the start of administration, thereby further supporting the preventive and/or therapeutic effects of tranilast against dysmenorrhea and/or associated symptoms thereof.

Furthermore, the backgrounds of Subjects C, D, E, F and G are as indicated below.

Background of Subject C

Subject C was a married woman in her thirties who had never been pregnant, never given birth and was suffering from organic dysmenorrhea.

Observed symptoms included intense lower abdominal pain, lower back pain and nausea during menstruation, and although she had been taking loxonin immediately prior to menstruation and about 4 to 5 voltaren tablets after the start of menstruation, she still had to be bedridden because of intolerable pain and to take off from work.

She began taking 100 mg of tranilast daily by oral administration three times a day on Sep. 20, 2008. She continued to take this daily for about 6 months until Mar. 21, 2009.

Background of Subject D

Subject D was a married woman in her early forties who had never been pregnant and never given birth and was suffering from organic dysmenorrhea.

Observed symptoms included intense lower abdominal pain and lower back pain during menstruation, and although she had been taking voltaren during menstruation, she continued to suffer from intense pain.

She began taking 100 mg of tranilast daily by oral administration three times per day on Nov. 18, 2008. She continued to take this daily for about six months until May 18, 2009.

Background of Subject E

Subject E was a married woman in her late thirties who had been pregnant once and given birth once, and was suffering from organic dysmenorrhea.

Observed symptoms included intense lower abdominal pain and lower back pain during menstruation, and she had been taking the low-dose oral contraceptive, Ortho M-21 tablets, since August 2007 until just prior to the study. She began taking 100 mg of tranilast daily by oral administration three times per day on Oct. 17, 2008. She continued to take this daily for about six months until Apr. 29, 2009.

Background of Subject F

Subject F was a married woman in her late thirties who had been pregnant 4 times and given birth 3 times, and who was suffering from organic dysmenorrhea.

Observed symptoms included intense lower abdominal pain and lower back pain during menstruation, and the pain was so intense that she was forced to take an analgesic every 4 to 5 hours. She began taking 100 mg of tranilast daily by oral administration three times per day on Apr. 9, 2009. She continued to take this daily for about six months until October 7, 2009.

Background of Subject G

Subject G was a married woman in her early forties who had been pregnant twice and given birth twice, and who was suffering from functional dysmenorrhea.

Observed symptoms included intense lower abdominal pain and lower back pain during menstruation. Since she was unable to endure the pain by taking over-the-counter analgesics, she was examined by a gynecologist, and thereafter although she had been taking prescription medicine, voltaren, she continued to suffer from continuing pain as well as adverse side effects.

She began taking 100 mg of tranilast daily by oral administration three times per day on May 14, 2009. She continued to take this daily for about seven months until Dec. 20, 2009.

Example 4

Clinical Study of Therapeutic Effect of Oral Administration of Tranilast (4)

Tranilast was orally administered to a Subject H suffering from dysmenorrhea to evaluate the preventive and/or therapeutic effects of tranilast on dysmenorrhea and/or associated symptoms thereof.

Background of Subject H

Subject H was a married woman in her thirties who had been pregnant three times and given birth twice, and who was suffering from organic dysmenorrhea.

Observed symptoms included intense lower abdominal pain and lower back pain during menstruation as well as chronically intense lower abdominal pain and lower back pain when not menstruating. Although she had been taking four tablets of loxonin per day for pain relief during menstruation in April 2010, since she continued to experience pain, she was examined as an out-patient by a gynecologist.

She began taking 100 mg of tranilast daily by oral administration three times per day on Apr. 21, 2010.

Pain diminished and she no longer need to take an analgesic at the time of her menstrual period roughly one month after beginning administration of tranilast. She was again examined as an out-patient by a gynecologist on May 28, 2010. A table comparing interview findings obtained by the gynecological specialist at that time with the interview findings obtained in the same way prior to beginning administration of tranilast are shown in FIG. 11.

Example 5

Clinical Study of Therapeutic Effect of Oral Administration of Tranilast (5)

Tranilast was orally administered to a Subject I suffering from dysmenorrhea to evaluate the preventive and/or therapeutic effects of tranilast on dysmenorrhea and/or associated symptoms thereof.

Background of Subject I

Subject I was a single women in her thirties who had never been pregnant and never given birth, and who was suffering from organic dysmenorrhea.

Observed symptoms include intense lower abdominal pain and lower back pain during menstruation as well as chronically intense lower abdominal pain and lower back pain when not menstruating.

The past history of Subject I was as indicated below.

Underwent surgery for excision of an ovarian lesion in 2003. Administered nasanyl, a GnRH analog, following surgery.

Began administration of suprecur, also a GnRH analog, in April 2009. Administration discontinued four months later due to increased γGTP levels.

Administration of suprecur resumed in February 2010. Administration subsequently discontinued due to appearance of low estrogen symptoms.

Began administration of the progesterone preparation, dienogest, on Mar. 18, 2010. Administration subsequently discontinued on April 27 due to persistent abnormal genital bleeding starting on April 7.

Subject I began taking 100 mg of tranilast daily by oral administration three times per day on May 14, 2010.

Although Subject I was in extreme pain, was barely able to go to work (she could barely get out of bed), and there were multiple days when she needed to take four analgesic tablets per day prior to the start of administration of tranilast, the pain diminished and improved to the extent that she only needed to take one tablet of analgesic per day for 3 days at the time of her first menstrual period after beginning administration of tranilast. She was subsequently examined as an out-patient by a gynecologist on Jun. 4, 2010. At that time, interview findings were obtained from Subject I that indicated that, since she is unable to take off from work due to the nature of her job, she was pleased that the menstrual pain during menstruation as well as chronic pelvic pain that she had experienced when not menstruating had diminished and no longer interfered with her job.

INDUSTRIAL APPLICABILITY

The drug of the present invention is useful as a prophylactic and/or therapeutic agent for dysmenorrhea and/or associated symptoms thereof.

The invention claimed is:

1. A method for treating functional dysmenorrhea, comprising administering to a subject in need thereof a pharmaceutical composition comprising, as an active ingredient thereof, tranilast or a salt thereof.

2. A method for inducing a transition of an endometrial epithelial cell from a mesenchymal form to an epithelial form, comprising administering to a subject suffering from functional dysmenorrhea in need thereof a pharmaceutical composition comprising, as an active ingredient, tranilast or a salt thereof.

3. A method of treating a recurrence of functional dysmenorrhea, comprising administering to a subject in need thereof a pharmaceutical composition comprising, as an active ingredient thereof, tranilast or a salt thereof.

4. The method according to claim 1, wherein the pharmaceutical composition is administered to the subject orally one to three times a day at a dosage of 50 to 1000 mg of active ingredient per day continuously for at least one month.

5. The method according to claim 1, wherein the pharmaceutical composition is administered to the subject orally one to three times a day at a dosage of 100 to 300 mg of active ingredient per day continuously for at least one month.

* * * * *